United States Patent
Miyazaki et al.

(10) Patent No.: US 10,497,152 B2
(45) Date of Patent: Dec. 3, 2019

(54) X-RAY CT APPARATUS AND RECONSTRUCTION PROCESSING APPARATUS

(71) Applicant: Canon Medical Systems Corporation, Otawara-shi (JP)

(72) Inventors: Hiroaki Miyazaki, Otawara (JP); Hiroaki Nakai, Nasushiobara (JP); Naoki Sugihara, Nasushiobara (JP); Tooru Kato, Nasushiobara (JP); Mikihito Hayashi, Otawara (JP); Emi Tamura, Yokohama (JP)

(73) Assignee: Canon Medical Systems Corporation, Otawara-shi (JP)

( * ) Notice: Subject to any disclaimer, the term of this patent is extended or adjusted under 35 U.S.C. 154(b) by 138 days.

(21) Appl. No.: 15/877,840

(22) Filed: Jan. 23, 2018

(65) Prior Publication Data

US 2018/0211417 A1 Jul. 26, 2018

(30) Foreign Application Priority Data

Jan. 24, 2017 (JP) .................. 2017-010413
Jan. 24, 2017 (JP) .................. 2017-010414
Dec. 27, 2017 (JP) .................. 2017-251527

(51) Int. Cl.
*A61B 6/03* (2006.01)
*G06T 11/00* (2006.01)
(Continued)

(52) U.S. Cl.
CPC ............ *G06T 11/005* (2013.01); *A61B 6/032* (2013.01); *A61B 6/461* (2013.01); *A61B 6/5205* (2013.01);
(Continued)

(58) Field of Classification Search
CPC ... A61B 6/4233; A61B 6/4241; A61B 6/4266; A61B 6/4275
See application file for complete search history.

(56) References Cited

U.S. PATENT DOCUMENTS 7,532,703 B2   5/2009  Du et al.
7,613,274 B2  11/2009  Tkaczyk et al.
(Continued)

FOREIGN PATENT DOCUMENTS

JP    2016-19725    2/2016

*Primary Examiner* — David P Porta
*Assistant Examiner* — Mamadou Faye
(74) *Attorney, Agent, or Firm* — Oblon, McClelland, Maier & Neustadt, L.L.P.

(57) ABSTRACT

An X-ray CT apparatus according to an embodiment includes an X-ray tube, a photon counting detector, and a processing circuitry. The X-ray tube is configured to generate X-rays. The photon counting detector includes a plurality of detecting elements each configured to output a signal in response to any of the X-rays becoming incident thereto after having passed through an examined subject. The processing circuitry is configured to determine, within a reconstruction region, a first region on which a spectrum reconstructing process is to be performed and a second region on which an energy integral reconstructing process is to be performed, on the basis of output values related to energy spectra based on the signals output by the detecting elements. The processing circuitry is configured to generate an image on the basis of the determined first region and the determined second region.

20 Claims, 17 Drawing Sheets

(51) Int. Cl.
   *A61B 6/00* (2006.01)
   *G06T 7/11* (2017.01)
   *G06T 7/136* (2017.01)
   *G01N 23/046* (2018.01)

(52) U.S. Cl.
   CPC .............. *G01N 23/046* (2013.01); *G06T 7/11* (2017.01); *G06T 7/136* (2017.01); *G06T 11/006* (2013.01); *A61B 6/4241* (2013.01); *G01N 2223/401* (2013.01); *G01N 2223/419* (2013.01); *G06T 2207/10081* (2013.01)

(56) References Cited

U.S. PATENT DOCUMENTS

| | | |
|---|---|---|
| 8,160,200 B2 | 4/2012 | Tkaczyk et al. |
| 2015/0038839 A1 | 2/2015 | Schaefer et al. |
| 2015/0117593 A1 | 4/2015 | Ji et al. |
| 2016/0070005 A1 | 3/2016 | Sagoh |
| 2016/0095559 A1 | 4/2016 | Gagnon et al. |
| 2017/0238896 A1* | 8/2017 | Iwai .................. A61B 6/542 |

\* cited by examiner

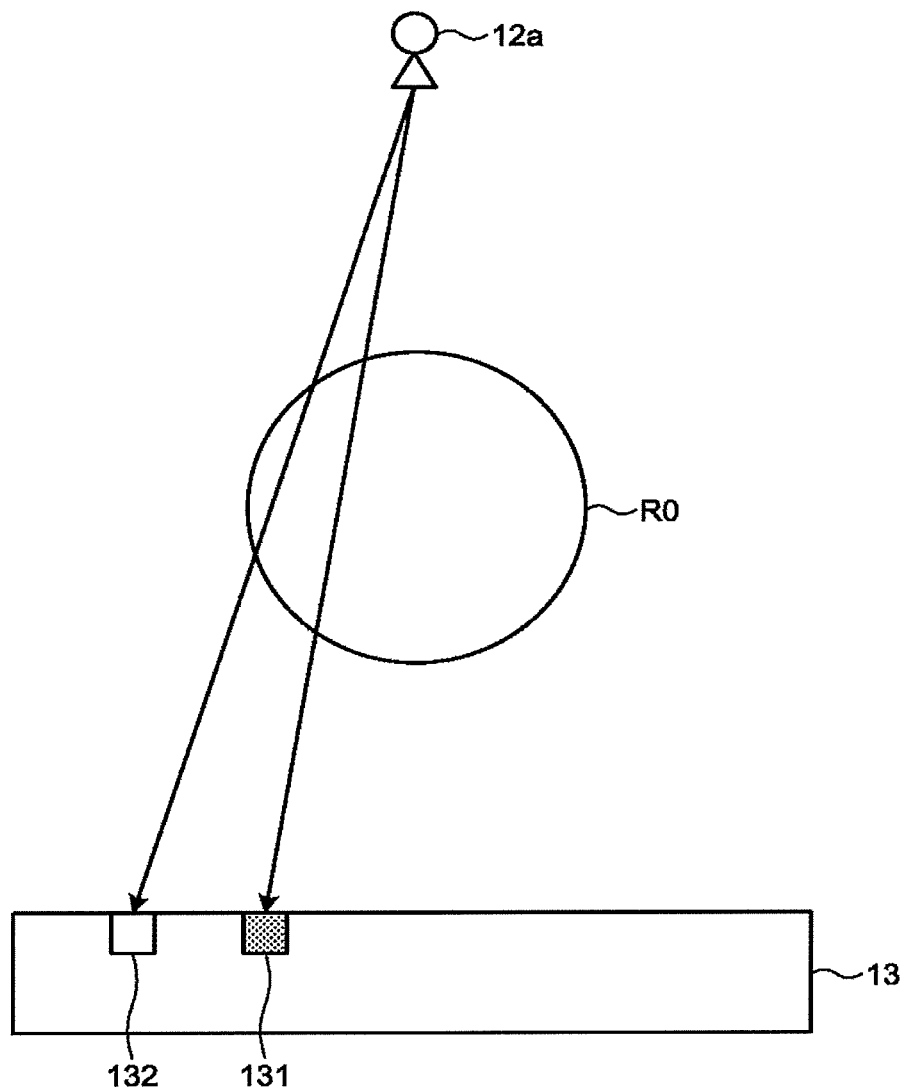

X-RAY CT APPARATUS AND RECONSTRUCTION PROCESSING APPARATUS

CROSS-REFERENCE TO RELATED APPLICATIONS

This application is based upon and claims the benefit of priority from Japanese Patent Application No. 2017-010413, filed on Jan. 24, 2017, Japanese Patent Application No. 2017-010414, filed on Jan. 24, 2017 and Japanese Patent Application No. 2017-251527, filed on Dec. 27, 2017; the entire contents of which are incorporated herein by reference.

FIELD

Embodiments described herein relate generally to an X-ray Computed Tomography (CT) apparatus and a reconstruction processing apparatus.

BACKGROUND

With X-ray Computed Tomography (CT) apparatuses, a technique called photon counting CT is known by which an image is rendered by counting the quantity of X-ray photons. During a photon counting CT procedure, an X-ray detector of a photon counting type (hereinafter, "photon counting X-ray detector") is used. The photon counting X-ray detector is configured to measure intensities of X-rays by counting the quantity of X-ray photons that have become incident thereto. Further, the photon counting X-ray detector is configured to measure the energy level of each of the X-ray photons, by using the notion that, when each X-ray photon is converted into an electric charge, the amount of electric charge occurring corresponds to the energy which the X-ray photon has. Accordingly, by performing the photon counting CT procedure, it is possible to obtain an energy spectrum indicating a distribution of quantities of photons corresponding to the energy levels.

BRIEF DESCRIPTION OF THE DRAWINGS

FIG. 3 is another drawing for explaining the process performed by the judging function according to the first embodiment;

DETAILED DESCRIPTION

It is an object of the present disclosure to provide an X-ray CT apparatus and a reconstruction processing apparatus capable of improving the precision level and the processing speed of an image reconstructing process performed in a photon counting Computed Tomography (CT) procedure.

An X-ray CT apparatus according to an embodiment includes an X-ray tube, a photon counting detector, and processing circuitry. The X-ray tube is configured to generate X-rays. The photon counting detector includes a plurality of detecting elements each configured to output a signal in response to any of the X-rays becoming incident thereto after having passed through an examined subject. The processing circuitry is configured to determine, within a reconstruction region, a first region on which a spectrum reconstructing process is to be performed and a second region on which an energy integral reconstructing process is to be performed, on the basis of output values related to energy spectra based on the signals output by the detecting elements. The processing circuitry is configured to generate an image on the basis of the determined first region and the determined second region.

Exemplary embodiments of an X-ray Computed Tomography (CT) apparatus and a reconstruction processing apparatus will be explained below, with reference to the accompanying drawings. Possible embodiments are not limited to the embodiments described below. Further, the contents of each of the embodiments are, in principle, similarly applicable to any other embodiment.

The X-ray CT apparatuses described in the embodiments below are each an apparatus capable of executing a photon counting CT procedure. In other words, the X-ray CT apparatuses described in the embodiments below are each an apparatus capable of reconstructing X-ray CT image data having a high Signal-to-Noise (S/N) ratio, by counting X-rays that have passed through an examined subject while using, not a conventional integral detector (that implements a current mode measuring method), but a detector that implements a photon counting method.

First Embodiment

Figure 1:
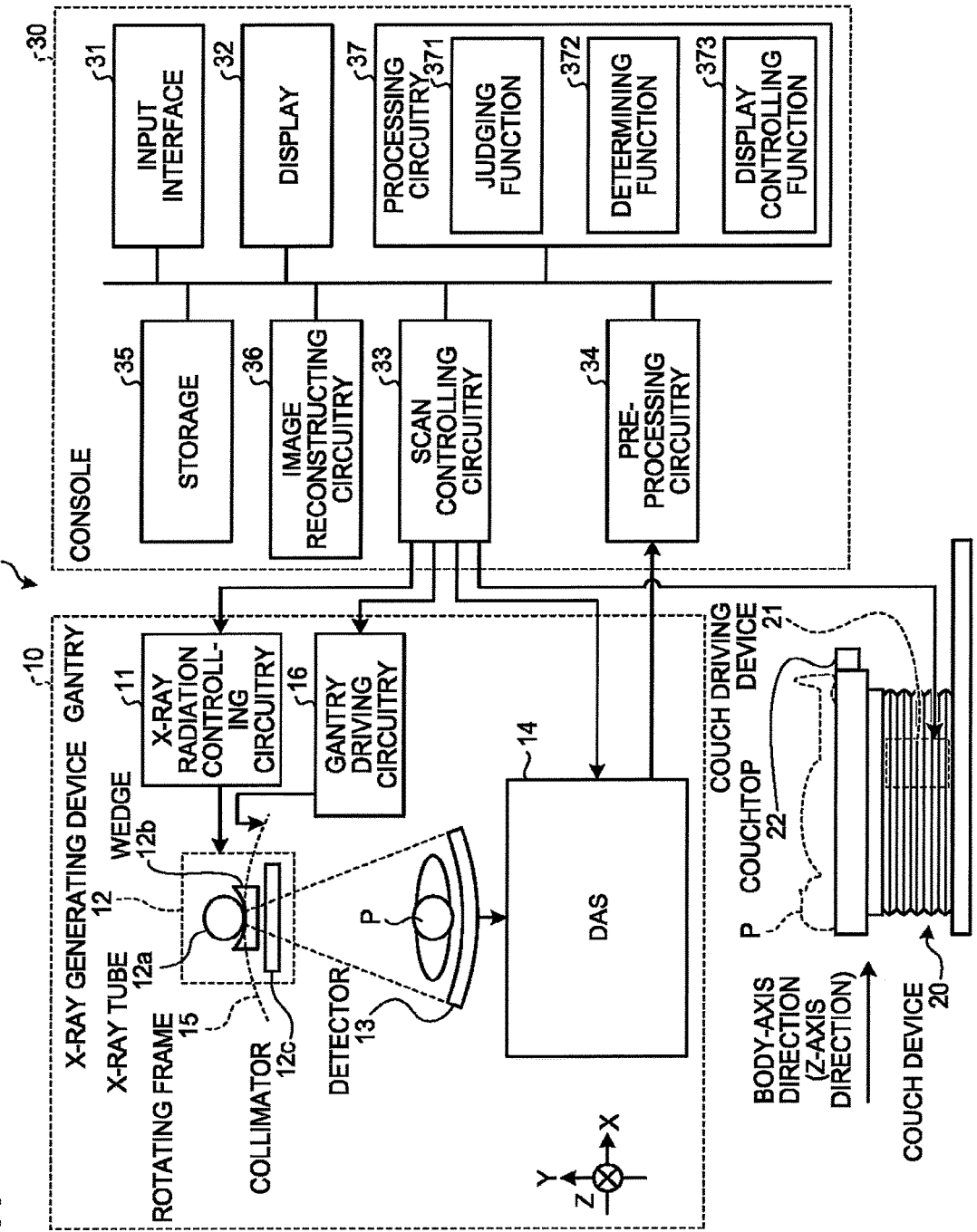
FIG. 1 is a block diagram illustrating an exemplary configuration of an X-ray CT apparatus according to a first embodiment.

FIG. 1 is a block diagram illustrating an exemplary configuration of an X-ray CT apparatus according to a first embodiment. As illustrated in FIG. 1, an X-ray CT apparatus 1 according to the first embodiment includes a gantry 10, a couch device 20, and a console 30.

The gantry 10 is a device configured to radiate X-rays onto an examined subject P (hereinafter, "patient"), to detect X-rays that have passed through the patient P, and to output data corresponding to the detected X-rays to the console 30. The gantry 10 includes X-ray radiation controlling circuitry 11, an X-ray generating device 12, a detector 13, DAS 14, a rotating frame 15, and gantry driving circuitry 16.

The X-ray radiation controlling circuitry 11 is a device configured to supply a high voltage to an X-ray tube 12a, as a high-voltage generating unit. The X-ray tube 12a is configured to generate X-rays by using the high voltage supplied thereto from the X-ray radiation controlling circuitry 11. The X-ray radiation controlling circuitry 11 is configured to adjust the X-ray dose radiated onto the patient P, by adjusting the X-ray tube voltage and/or the X-ray tube current supplied to the X-ray tube 12a, under control of scan controlling circuitry 33 (explained later).

Further, the X-ray radiation controlling circuitry 11 is configured to perform a switching process on a wedge 12b. Further, by adjusting the opening degree of a collimator 12c, the X-ray radiation controlling circuitry 11 is configured to adjust the radiation range (a fan angle or a cone angle) of the X-rays. In the present embodiment, an arrangement is acceptable in which an operator manually switches among a plurality of types of wedges.

The X-ray generating device 12 is a device configured to generate the X-rays and to radiate the generated X-rays onto the patient P. The X-ray generating device 12 includes the X-ray tube 12a, the wedge 12b, and a collimator 12c.

The X-ray tube 12a is a vacuum tube configured to radiate an X-ray beam onto the patient P by using the high voltage supplied thereto by the X-ray radiation controlling circuitry 11. The X-ray tube 12a radiates the X-ray beam onto the patient P, as the rotating frame 15 rotates. The X-ray tube 12a is configured to generate the X-ray beam that spreads with the fan angle or the cone angle. For example, under the control of the X-ray radiation controlling circuitry 11, the X-ray tube 12a is capable of continuously emitting X-rays in the entire surrounding of the patient P to realize a full reconstruction process and is capable of continuously emitting X-rays in an emission range (180 degrees+the fan angle) that enables a half reconstruction to realize a half reconstruction process. Further, under the control of the X-ray radiation controlling circuitry 11, the X-ray tube 12a is capable of intermittently emitting X-rays (pulse X-rays) in positions (X-ray tube positions) set in advance. Further, the X-ray radiation controlling circuitry 11 is also capable of modulating the intensities of the X-rays emitted from the X-ray tube 12a. For example, the X-ray radiation controlling circuitry 11 increases the intensities of the X-rays emitted from the X-ray tube 12a in a specific X-ray tube position and decreases the intensities of the X-rays emitted from the X-ray tube 12a in a range other than the specific X-ray tube position.

The wedge 12b is an X-ray filter configured to adjust the X-ray dose of the X-rays emitted from the X-ray tube 12a. More specifically, the wedge 12b is a filter configured to pass and attenuate the X-rays emitted from the X-ray tube 12a, so that the X-rays radiated from the X-ray tube 12a onto the patient P have a predetermined distribution. For example, the wedge 12b is a filter obtained by processing aluminum so as to have a predetermined target angle and a predetermined thickness. The wedge may be referred to as a wedge filter or a bow-tie filter.

The collimator 12c is configured by using a lead plate or the like and has a slit in a part thereof. For example, by using the slit, the collimator 12c is configured to narrow down the radiation range of the X-rays of which the X-ray dose has been adjusted by the wedge 12b, under the control of the X-ray radiation controlling circuitry 11 (explained later).

The detector 13 is a detector of a photon counting type (hereinafter, "photon counting detector") that includes a plurality of detecting elements each configured to output a signal in response to any of the X-rays becoming incident thereto after having passed through the patient P. The detecting elements are each configured to output, every time an X-ray photon becomes incident thereto, a signal that makes it possible to measure an energy value of the X-ray photon. For example, the X-ray photon is a photon of an X-ray that was radiated from the X-ray tube 12a and has passed through the patient P. Each of the detecting elements is configured to output an electrical signal (an analog signal) corresponding to one pulse every time an X-ray photon becomes incident thereto.

Each of the detecting elements described above is structured, for example, by using a scintillator and an optical sensor such as a photomultiplier. In that situation, the detector 13 illustrated in FIG. 1 serves as a detector of an indirect conversion type configured to convert the X-ray photons that have become incident thereto, into scintillator light, by using the scintillators and to further convert the scintillator light into the electrical signals by using the optical sensors such as the photomultipliers. Alternatively, for example, each of the detecting elements described above may be a semiconductor element configured by using cadmium telluride (CdTe) or cadmium zinc telluride (CdZnTe). In that situation, the detector 13 illustrated in FIG. 1 serves as a detector of a direct conversion type configured to directly convert the X-ray photons that have become incident thereto, into electrical signals.

For example, the detector 13 illustrated in FIG. 1 may be a planar detector in which the detecting elements are arranged in N rows along the channel direction (the direction along the rotating direction of the detector 13) and in M rows along the axis of the rotation center of the rotating frame 15 (the Z-axis direction in FIG. 1) observed while the gantry 10 is not tilted. When a photon becomes incident thereto, each of the detecting elements outputs an electrical signal corresponding to one pulse. The X-ray CT apparatus 1 is capable of counting the quantity of X-ray photons that have become incident to the detecting elements, by discriminating the individual pulses output by the detecting elements. Further, by performing a computing process based on the intensities of the pulses, the X-ray CT apparatus 1 is capable of measuring energy values of the counted X-ray photons.

The DAS 14 has a function of acquiring a count result that is a result of the counting process using the output signals of the detector 13. The DAS 14 is an electrical circuit structured by using an amplifier configured to amplify the electrical signals output by the detecting elements, an Analog/Digital (A/D) converter configured to convert the electrical signals into digital signals, and the like. The DAS 14 is configured to count the photons (the X-ray photons) derived from the X-rays that were radiated from the X-ray tube 12a and have passed through the patient P and to acquire a result of discriminating the energy levels of the counted photons as the count result. For example, when X-rays are continuously emitted from the X-ray tube 12a while the rotating frame 15 is rotating, the DAS 14 acquires count results corresponding to the entire surrounding (corresponding to 360 degrees). Further, the DAS 14 transmits the count results to the console 30. The DAS 14 may be referred to as a Data Acquisition System (DAS). The DAS 14 is sometimes called data acquiring circuitry.

For example, the DAS 14 acquires, for each of various positions of the X-ray tube 12a (X-ray tube positions), a count result represented by incident positions (detection positions) of the X-ray photons that were counted by discriminating the pulses output by the detecting elements and an energy value of the X-ray photons. The incident positions are each the position of a detecting element observed when the pulse used for the counting was output. Further, the DAS 14 calculates the energy value from peak values of the pulses and a response function unique to the system. Alternatively, the DAS 14 may calculate the energy value by, for example, integrating the intensities of the pulses. The DAS 14 distributes the calculated energy values into a plurality of energy discriminatory zones (energy bins) by using a comparator, for example. The count results that have been distributed into the plurality of energy discriminatory zones (the energy bins) form an energy spectrum indicating a distribution of quantities of photons corresponding to the energy levels.

The rotating frame 15 is an annular frame configured to support the X-ray generating device 12 and the detector 13 so as to oppose each other while the patient P is interposed therebetween. The rotating frame 15 is configured to be rotated by the gantry driving circuitry 16 (explained later) at a high speed on a circular orbit centered on the patient P.

The gantry driving circuitry 16 is configured to cause the X-ray generating device 12 and the detector 13 to revolve on the circular orbit centered on the patient P, by driving the rotating frame 15 to rotate. For example, the gantry driving circuitry 16 is structured with: a power transmission mechanism such as a motor used for driving the rotating frame 15 to rotate; and a processor configured to control operations of the power transmission mechanism.

The couch device 20 is a device on which the patient P is placed and includes a couch driving device 21 and a couchtop 22, as illustrated in FIG. 1. The couch driving device 21 is configured to move the patient P into the rotating frame 15 by moving the couchtop 22 in the Z-axis direction. The couchtop 22 is a board on which the patient P is placed. In the present embodiment, an example will be explained in which the relative position between the gantry 10 and the couchtop 22 can be changed by controlling the couchtop 22; however, possible embodiments are not limited to this example. For instance, when the gantry 10 is self-propelled, the relative position between the gantry 10 and the couchtop 22 may be changed by controlling the self-propelled movement of the gantry 10.

Further, for example, the gantry 10 performs a helical scan by which the patient P is helically scanned by causing the rotating frame 15 to rotate while the couchtop 22 is being moved. In another example, the gantry 10 performs a conventional scan by which the patient P is scanned on a circular orbit by causing the rotating frame 15 to rotate, while the position of the patient P is being fixed after the couchtop 22 is moved. In yet another example, the gantry 10 implements a step-and-shoot method by which the conventional scan is performed in multiple scan areas, by moving the position of the couchtop 22 at regular intervals.

The console 30 is a device configured to receive operations performed by the operator on the X-ray CT apparatus 1 and also configured to reconstruct X-ray CT image data by using projection data acquired by the gantry 10. As illustrated in FIG. 1, the console 30 includes an input interface 31, a display 32, the scan controlling circuitry 33, pre-processing circuitry 34, a storage 35, image reconstructing circuitry 36, and processing circuitry 37.

The input interface 31 includes a mouse, a keyboard, a trackball, a switch, a button, a joystick, and/or the like used by the operator of the X-ray CT apparatus 1 to input various types of instructions and various types of settings. The input interface 31 is configured to transfer information about the instructions and the settings received from the operator to the processing circuitry 37. For example, the input interface 31 receives, from the operator, an image taking condition for the X-ray CT image data, a reconstruction condition used when the X-ray CT image data is reconstructed, an image processing condition applied to the X-ray CT image data, and the like.

The display 32 is a monitor referenced by the operator. The display 32 is configured to display image data generated from the X-ray CT image data for the operator and to display a Graphical User Interface (GUI) used for receiving the various types of instructions and the various types of settings from the operator via the input interface 31, under control of the processing circuitry 37.

The scan controlling circuitry 33 is a processor that is configured, under the control of the processing circuitry 37, to realize a function of controlling the data acquiring process performed by the gantry 10, by controlling operations of the X-ray radiation controlling circuitry 11, the gantry driving circuitry 16, the DAS 14, and the couch driving device 21.

The pre-processing circuitry 34 is a processor configured to realize a function of generating corrected projection data by performing a logarithmic converting process as well as correcting processes such as an offset correcting process, a sensitivity correcting process, a beam hardening correcting process, and the like, on the count results generated by the DAS 14.

The storage 35 is configured by using a Not AND (NAND) flash memory or a Hard Disk Drive (HDD), for example, and is configured to store therein the projection data generated by the pre-processing circuitry 34. Further, the storage 35 is also configured to store therein image data and the like generated by the image reconstructing circuitry 36 (explained later). Also, the storage 35 is configured to store therein processing results obtained by the processing circuitry 37 (explained later), as necessary.

The image reconstructing circuitry 36 is a processor configured to realize a function of generating the X-ray CT image data on the basis of the signals output by the detector 13. The image reconstructing circuitry 36 reconstructs the X-ray CT image data by performing, for example, a back projection process on the projection data stored in the storage 35. Examples of the back projection process include a back projection process using a Filtered Back Projection (FBP) method. Alternatively, the image reconstructing circuitry 36 may perform the reconstructing process by using a successive approximation method, for example. Further, the image reconstructing circuitry 36 is configured to generate the image data by performing various types of image processing processes on the X-ray CT image data. The image reconstructing circuitry 36 stores the reconstructed X-ray CT image data and the image data generated by performing the various types of image processing processes, into the storage 35. The image reconstructing circuitry 36 is an example of a reconstructing unit. The image reconstructing circuitry 36 is also an example of the image generating unit.

In the present example, the projection data generated from the count results obtained in the photon counting CT procedure includes information about the energy spectra of the X-rays that were attenuated as a result of having passed through the patient P. For this reason, the image reconstructing circuitry 36 is able to reconstruct, for example, X-ray CT image data (energy discriminatory image data) in which a specific energy component is rendered in the image. Further, the image reconstructing circuitry 36 is capable of reconstructing, for example, X-ray CT image data of each of a plurality of energy components.

Further, for example, the image reconstructing circuitry 36 is capable of generating image data in which a plurality of pieces of X-ray CT image data are superimposed on one another, by assigning a color tone corresponding to an energy component to each of the pixels in the X-ray CT image data representing various energy components, so as to color-code the pixels in accordance with the energy components. Further, by using k-absorption edges that are each unique to a substance, the image reconstructing circuitry 36 is capable of generating image data that makes it possible to identify various substances. Examples of other types of image data that can be generated by the image reconstructing circuitry 36 include monochrome X-ray image data, density image data, and effective atomic number image data. A process of reconstructing X-ray CT image data such as energy discriminatory image data, substance discriminatory image data, monochrome X-ray image data, density image data, effective atomic number image data, and/or the like will be referred to as a "spectrum reconstructing process".

The processing circuitry 37 is configured to exercise overall control of the X-ray CT apparatus 1 by controlling operations of the gantry 10, the couch device 20, and the console 30. More specifically, the processing circuitry 37 is configured to control a CT scan performed by the gantry 10, by controlling the scan controlling circuitry 33. Also, the processing circuitry 37 is configured to control the image reconstructing process and the image generating process performed by the console 30, by controlling the image reconstructing circuitry 36. Further, the processing circuitry 37 is configured to exercise control so that the display 32 displays any of the various types of image data stored in the storage 35.

Further, as illustrated in FIG. 1, the processing circuitry 37 is configured to execute a judging function 371, a determining function 372, and a display controlling function 373. In this situation, for example, processing functions executed by the constituent elements of the processing circuitry 37 illustrated in FIG. 1, namely the functions such as the judging function 371, the determining function 372, and the display controlling function 373 are recorded in the storage 35 in the form of computer-executable programs. The processing circuitry 37 is a processor, for example, and by reading and executing the computer programs (hereinafter, "programs"), the processing circuitry 37 is configured to realize the functions corresponding to the read programs. In other words, the processing circuitry 37 that has read the programs has the functions illustrated within the processing circuitry 37 in FIG. 1. Details of the judging function 371, the determining function 372, and the display controlling function 373 will be explained later.

An overall configuration of the X-ray CT apparatus 1 according to the first embodiment has thus been explained. With this configuration, the X-ray CT apparatus 1 according to the first embodiment is configured to reconstruct the X-ray CT image data by performing the photon counting CT procedure.

Incidentally, during the photon counting CT procedure, the absorption amount of X-rays is larger in a center part of the patient P, whereas the quantity of X-ray photons that become incident to the detector is smaller. For this reason, because it is possible to accurately obtain an energy spectrum of the projection data derived from the passing through the center part of the patient P, it is possible to obtain a reconstruction image having a high level of precision. In contrast, in perimeter parts of the patient P or sites having lower levels of X-ray absorption, because the quantity of X-ray photons that become incident to the detector is larger, a phenomenon called "pile up" may occur in some situations. The "pile up" is a phenomenon in which, when the quantity of X-ray photons that become incident per unit time period increases, waveforms generated by the X-ray photons overlap each other, and some of the X-ray photons fail to be counted. When the energy spectra are inaccurate in this manner, not only the reconstructed image is inaccurate, but also it is difficult to restore the energy spectra, and there is a possibility that the processing time period becomes extremely long.

To cope with this situation, the X-ray CT apparatus 1 according to the first embodiment executes the processing functions explained below, for the purpose of improving the precision level and the processing speed of the image reconstructing processes in the photon counting CT procedure.

The judging function 371 is configured to judge whether or not the output values related to the energy spectra based on the signals output by the detecting elements are each equal to or larger than a threshold value. For example, the judging function 371 calculates, for each of the views, the output values related to the energy spectra by using the projection data stored in the storage 35. Further, the judging function 371 judges, for each of the views, whether or not the calculated output values of the view are each equal to or larger than the threshold value. After that, the judging function 371 outputs the judgment results regarding all the views, to the determining function 372. The judging function 371 is an example of the judging unit.

Processes performed by the judging function 371 will be explained with reference to FIGS. 2, 3, 4A, and 4B. FIGS. 2, 3, 4A, and 4B are drawings for explaining the processes performed by the judging function 371 according to the first embodiment.

For example, the judging function 371 reads the projection data from the storage 35. In this situation, the projection data stored in the storage 35 includes information about the energy spectra based on the signals output by the detecting elements in correspondence with the views. The judging function 371 calculates the output values for each of the views by using the energy spectra corresponding to the views.

Figure 2:
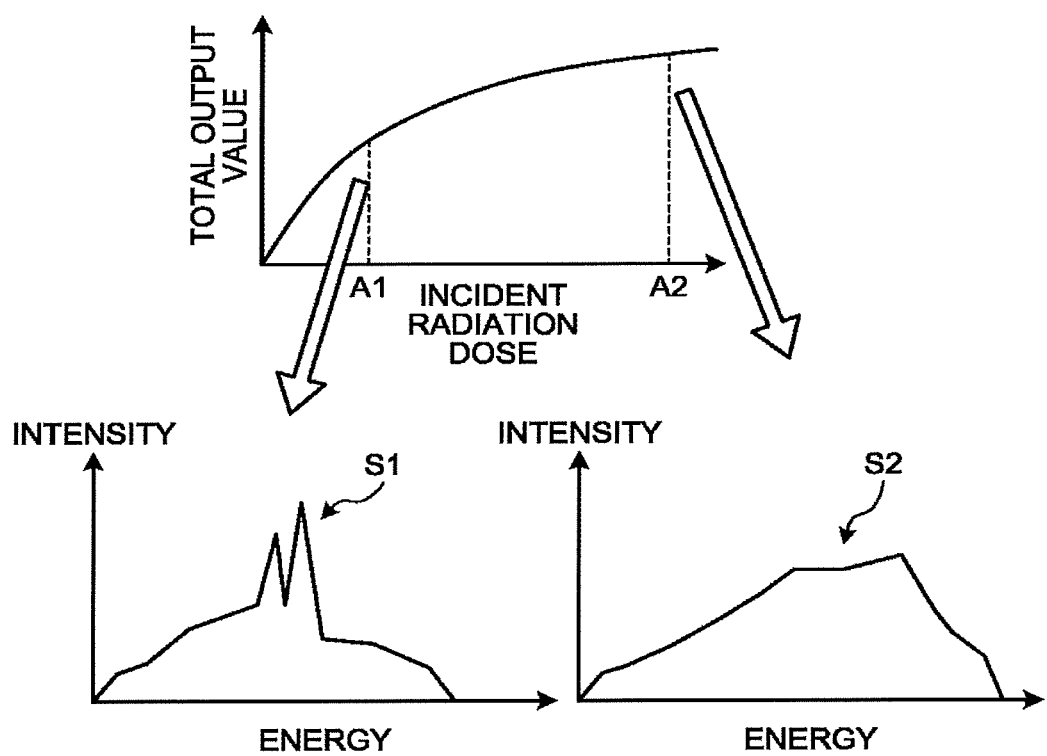
FIG. 2 is a drawing for explaining a process performed by a judging function according to the first embodiment.

The top section of FIG. 2 illustrates a relationship between incident radiation doses that have become incident in various detection positions (the positions of the detecting elements) in a certain view and output values. In this situation, when the incident radiation dose in the top section of FIG. 2 is A1, for instance, an X-ray energy spectrum S1 illustrated in the bottom left section of FIG. 2 is obtained. As another example, when the incident radiation dose in the top section of FIG. 2 is A2, for instance, an X-ray energy spectrum S2 illustrated in the bottom right section of FIG. 2 is obtained. By using the energy spectra corresponding to the various detection positions, the judging function 371 calculates the output values in the detection positions for each of the views. In other words, the judging function 371 calculates the output values for each of all the detected projection paths of the X-rays.

In this situation, the output values may be defined as any of first to fourth output values described below, for example. In the following sections, for the sake of convenience in the explanation, examples will be explained in which the X-ray tube voltage in the image taking condition for a main scan is set to 120 kVp, while the counts of the energy bins are expressed as Ci.

The first output value is a total output value of the counts of the energy bins. In that situation, the output value is expressed as $\Sigma C_i$ (where i=1 keV to 120 keV), for example. In other words, the judging function 371 calculates the total output value $\Sigma C_i$ (where i=1 keV to 120 keV) of the counts of the energy bins, as the output value. The reason why the counts equal to or smaller than 120 keV are used is that, in theory, it is considered impossible for such counts to be a count of piled-up signals (called "pile-up count").

The second output value is a pile-up count value of the count of the energy bins. In that situation, the output value is expressed as $\Sigma C_i$ (where i>120 keV), for example. In other words, the judging function 371 calculates the pile-up count values of the counts of the energy bins, as the output value. The reason why the counts that are larger than 120 keV are used is that, in theory, such counts are considered as pile-up counts.

The third output value is an energy integral value of representative values of the energy bins. In that situation, the output value is expressed as $\Sigma (C_i \times E_i)$ (where i=1 keV to 120 keV), for example. In other words, the judging function 371 calculates the energy integral value of the representative values of the energy bins as the output value. In this expression, Ei denotes a median (the representative value) of each energy bin.

The fourth output value is a pile-up energy integral value of representative values of the energy bins. In that situation, the output value is expressed as $\Sigma (C_i \times E_i)$ (where i>120 keV), for example. In other words, the judging function 371 calculates the pile-up energy integral value of the representative values of the energy bins, as the output value. In this expression, Ei denotes a median (the representative value) of each energy bin.

As explained above, the judging function 371 calculates one of the first to the fourth output values, as the output values related to the energy spectra. The explanations about the first to the fourth output values above are merely examples, and possible embodiments are not limited to these examples. For instance, the first output value may be defined as $\Sigma C_i$ (where i=1 keV to 115 keV) or may be defined as $\Sigma C_i$ (where i=1 keV to 125 keV). In other words, the intensities of the energy levels of the X-ray photons subject to the counting process do not necessarily have to match the X-ray tube voltage. It should be noted, however, that it is desirable to set the intensities of the energy levels of the X-ray photons subject to the counting process, on the basis of the X-ray tube voltage.

Further, for each of the views, the judging function 371 judges whether or not the calculated output values are each equal to or larger than the threshold value. For example, for each of the views, the judging function 371 judges whether or not the output value of each of the detecting elements is equal to or larger than the threshold value.

Figure 4A:
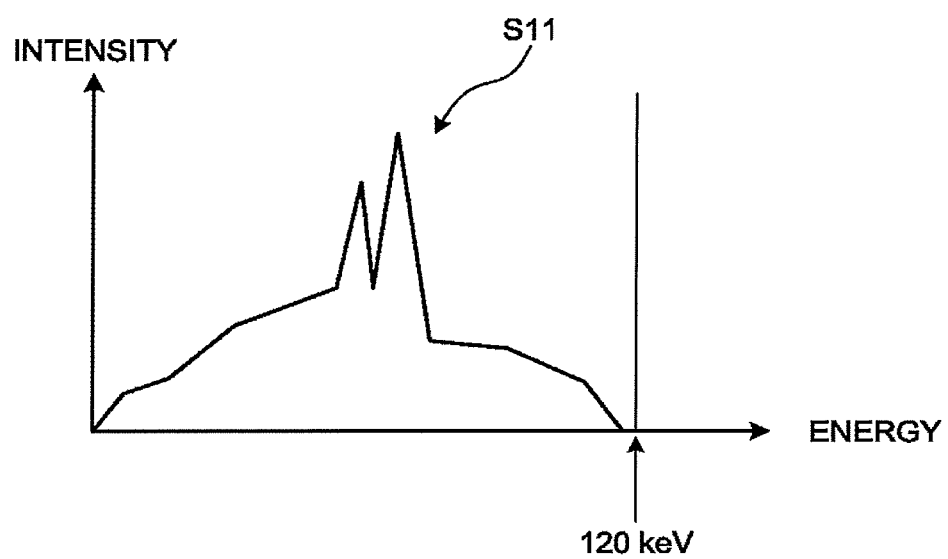
FIGS. 4A and 4B are other drawings for explaining the process performed by the judging function according to the first embodiment.
Figure 4B:
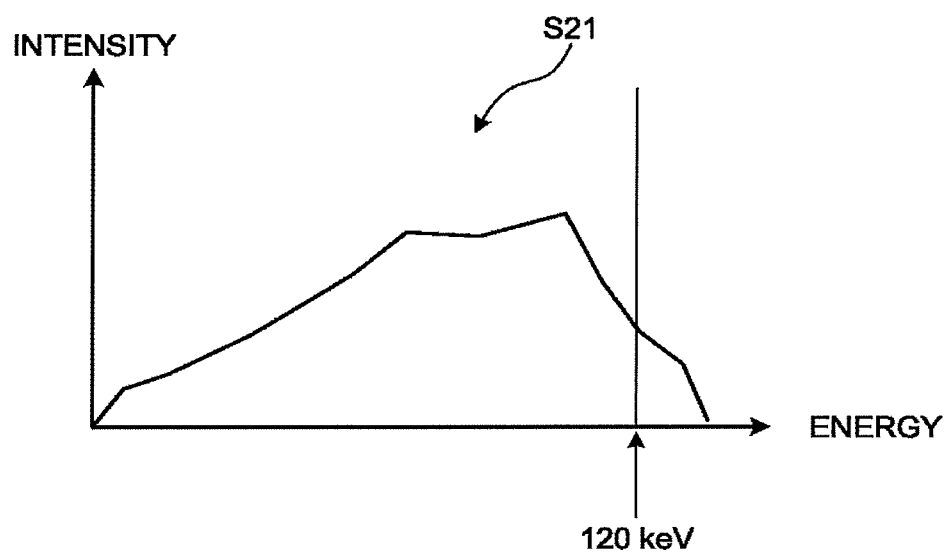

An example of the judging process performed by the judging function 371 will be explained, with reference to FIGS. 3, 4A, and 4B. FIG. 3 illustrates an example in which the X-rays radiated by the X-ray tube 12a in the 0-degree position are detected by detecting elements 131 and 132 included in the detector 13. Further, FIG. 4A illustrates an X-ray energy spectrum S11 corresponding to the detecting element 131. FIG. 4B illustrates an X-ray energy spectrum S21 corresponding to the detecting element 132. R0 denotes a reconstruction region.

As illustrated in FIG. 3, the detecting element 131 detects an X-ray that has passed through a position (a projection path) closer to the center part of the patient P, in comparison to the detecting element 132. The closer the position is to the center part of the patient P, the more X-rays are absorbed. Consequently, the energy spectrum S11 corresponding to the detecting element 131 does not contain energy equal to or higher than 120 keV (see FIG. 4A). In contrast, the energy spectrum S21 corresponding to the detecting element 132 contains energy equal to or higher than 120 keV (see FIG. 4B).

Further, with respect to each of the energy spectra S11 and S21, the judging function 371 judges whether or not the output value is equal to or larger than the threshold value. For example, when the second output value (the pile-up count) is calculated, the output value X1 of the energy spectrum S11 is "0" and is therefore smaller than the output value X2 of the energy spectrum S21. In this situation, when a threshold value Th satisfying "X1<Th<X2" is set, the judging function 371 determines that the output value X1 of the energy spectrum S11 is smaller than the threshold value Th, while the output value X2 of the energy spectrum S21 is equal to or larger than the threshold value Th. In the present example, for the sake of convenience in the explanation, the situation is explained in which the judging process is performed on the output values of the detecting elements 131 and 132 for the specific view. However, the judging function 371 performs the judging process on the output values of all the detecting elements corresponding to all the views. In other words, the judging function 371 judges whether or not the calculated output value is equal to or larger than the threshold value, with respect to each of all the detected projection paths of the X-rays.

As explained above, for each of the views, the judging function 371 judges whether or not the output value of each of the detecting elements is equal to or larger than the threshold value. The situations illustrated in FIGS. 3, 4A, and 4B are merely examples, and possible embodiments are not limited to the examples explained above. For instance, the threshold value Th above may arbitrarily be set. For example, when the threshold value Th is set to 0, it is possible to perform the judging process on the basis of whether there is a pile-up count or not. Further, it is also acceptable to measure a pile-up count value that has no impact on the processing time period required by the reconstructing process and to perform the judging process while permitting any values up to the measured pile-up count value. Further, the threshold value Th may be set to permit any values equal to or higher than a certain count rate, on the basis of a time constant of the circuit, or the like. In other words, the threshold value Th is a value that is set for the purpose of improving the precision level and the processing speed of the image reconstructing processes. Further, although the second output value is used in the above explanation, possible embodiments are not limited to this example. The judging function 371 is also able to perform the judging process by using any of the first, the third, and the fourth output values.

Further, generally speaking, the closer a position is to the center of the reconstruction region R0, the lower the count rate is. The closer a position is to the outer edge of the reconstruction region R0, the higher the count rate is. For this reason, for example, the judging function 371 may divide the reconstruction region R0 into a center region and an outer edge region on the basis of a scanogram image or information about the imaged site, so as to perform the judging process while selectively focusing on the outer edge region (or a region near the boundary between the center region and the outer edge region) where the energy spectra concerning a pile-up or the like may be inaccurate.

Within the reconstruction region, the determining function 372 is configured to determine a spectrum reconstruction region (a first region) on which a spectrum reconstructing process is to be performed and an energy integral reconstruction region (a second region) on which an energy integral reconstructing process is to be performed, on the basis of the judgment result obtained by the judging function 371. The determining function 372 is an example of the determining unit. In other words, the determining function 372 is configured to determine, within the reconstruction region, the first region on which the spectrum reconstructing process is to be performed and the second region on which the energy integral reconstructing process is to be performed, on the basis of the output values related to the energy spectra based on the signals output by the detecting elements.

In this situation, the spectrum reconstructing process is a process to reconstruct X-ray CT image data such as energy discriminatory image data, substance discriminatory image data, monochrome X-ray image data, density image data, effective atomic number image data, and/or the like, by using the count results obtained in the photon counting CT procedure. In contrast, the energy integral reconstructing process is a process to reconstruct an energy integral reconstruction image, by using the count results obtained in the photon counting CT procedure. More specifically, in the energy integral reconstructing process according to the first embodiment, the image reconstructing circuitry 36 calculates energy integral data by calculating either the sum (a total value) of the counts of the energy bins or the sum of products of representative values of the energy bins and the counts. After that, the image reconstructing circuitry 36 reconstructs the energy integral reconstruction image by using the calculated energy integral data.

For example, on the basis of the judgment result obtained by the judging function 371, the determining function 372 determines whether each of different positions (pixel positions) in the reconstruction region R0 is in the spectrum reconstruction region or the energy integral reconstruction region. More specifically, when the output values of all the views (paths) going through a certain position are smaller than the threshold value, the determining function 372 determines that the position is in the spectrum reconstruction region. Further, within the reconstruction region R0, the determining function 372 determines the region other than the spectrum reconstruction region as the energy integral reconstruction region. In other words, with respect to all the views going through a certain position, when there is at least one view of which the output value is equal to or larger than the threshold value, the determining function 372 determines that the position is in the energy integral reconstruction region. The determining process performed by the determining function 372 is not limited to the example described above. Other examples of the determining process will be explained later.

Figure 5:
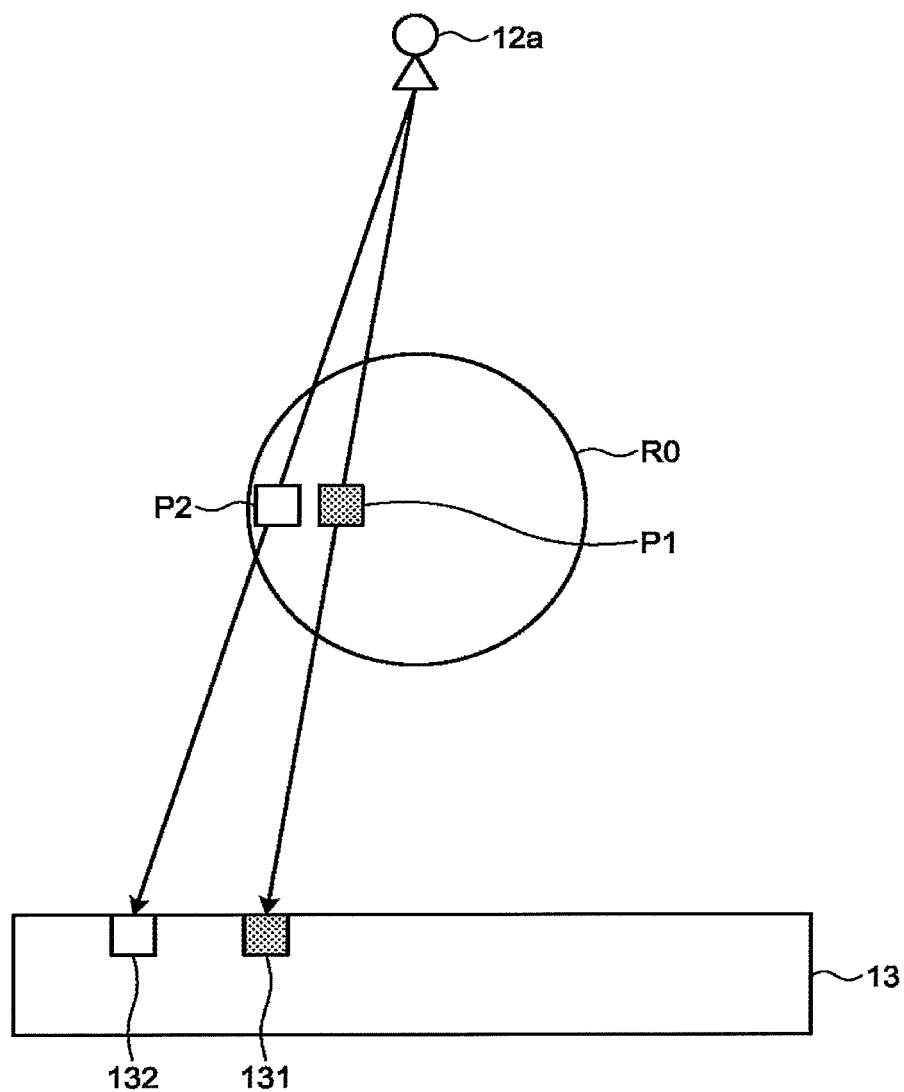
FIG. 5 is a drawing for explaining a process performed by a determining function according to the first embodiment.

An example of the determining process performed by the determining function 372 will be explained, with reference to FIGS. 5, 6, 7A, and 7B. As an example, FIG. 5 illustrates a situation where the determining process is performed with respect to positions P1 and P2 in the reconstruction region R0. The position P1 is on the projection path of an X-ray detected by the detecting element 131 illustrated in FIG. 5. The position P2 is on the projection path of an X-ray detected by the detecting element 132 illustrated in FIG. 5.

As illustrated in FIG. 5, for example, the determining function 372 refers to the judgment results obtained by the judging function 371, with respect to all the views going through the position P1. For the position P2 also, the determining function 372 similarly refers to the judgment results obtained by the judging function 371, with respect to all the views going through the position P2.

Figure 6:
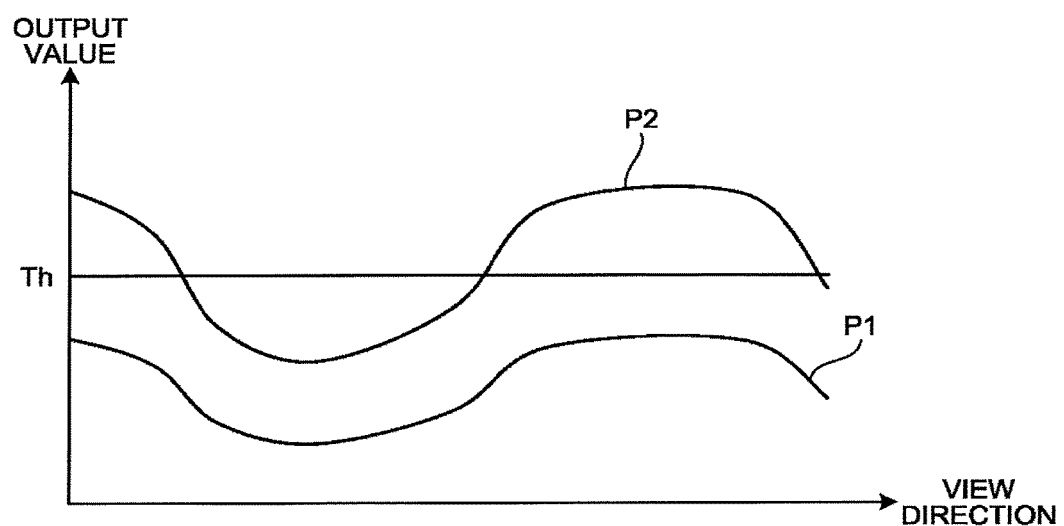
FIG. 6 is another drawing for explaining the process performed by the determining function according to the first embodiment.

FIG. 6 illustrates judgment results corresponding to all the views going through the positions P1 and P2. In FIG. 6, the vertical axis expresses output values, whereas the horizontal axis expresses view directions. Further, the threshold value Th is the threshold value used in the judging process performed by the judging function 371. In this situation, in the position P1, the output values corresponding to all the views are each smaller than the threshold value. Accordingly, the determining function 372 determines that the position P1 is in the spectrum reconstruction region. On the contrary, in the position P2, the output values corresponding to some of the views are each equal to or larger than the threshold value. Accordingly, the determining function 372 determines that the position P2 is in the energy integral reconstruction region. After that, for each of the other positions in the reconstruction region R0, the determining function 372 similarly determines whether the position is in the spectrum reconstruction region or the energy integral reconstruction region.

Figure 7A:
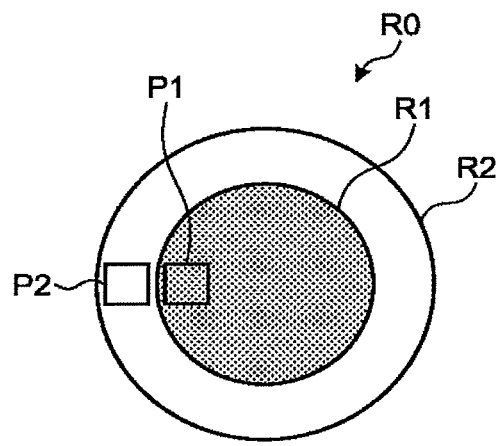
FIGS. 7A and 7B are other drawings for explaining the process performed by the determining function according to the first embodiment.
Figure 7B:
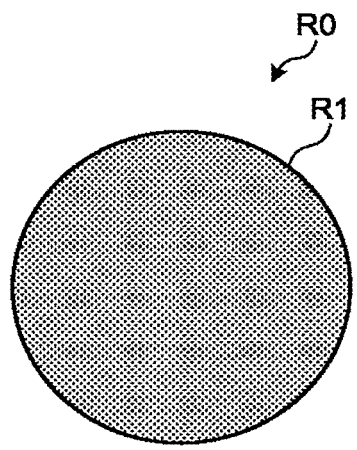

In the manner described above, with respect to each of the positions included in the reconstruction region R0, the determining function 372 determines whether the position is in the spectrum reconstruction region or the energy integral reconstruction region, on the basis of the judgment results regarding the views going through the positions. As a result, as illustrated in FIG. 7A, the determining function 372 determines, for example, a spectrum reconstruction region R1 and an energy integral reconstruction region R2 included in the reconstruction region R0. Further, when the output values corresponding to all the views going through all the positions are smaller than the threshold value, the determining function 372 determines the entirety of the reconstruction region R0 to be the spectrum reconstruction region R1, as illustrated in FIG. 7B.

After that, the determining function 372 outputs information indicating the spectrum reconstruction region R1 and the energy integral reconstruction region R2 that were determined, to the image reconstructing circuitry 36. Accordingly, for the spectrum reconstruction region R1, the image reconstructing circuitry 36 generates a spectrum reconstruction image by performing a spectrum reconstructing process. In contrast, for the energy integral reconstruction region R2, the image reconstructing circuitry 36 generates an energy integral reconstruction image by performing an energy integral reconstructing process. In other words, the image reconstructing circuitry 36 generates the images on the basis of the determination made by the determining function 372. That is to say, the image reconstructing circuitry 36 generates the images on the basis of the first region and the second region.

The situations illustrated in FIGS. 5, 6, 7A, and 7B are merely examples, and possible embodiments are not limited to these examples. For instance, although the example was explained with reference to FIG. 6 in which the constant threshold value is set for all the views, possible embodiments are not limited to this example. For instance, mutually-different threshold values may be set in correspondence with the views (the positions of the X-ray tube 12a). In that situation, the threshold value Th illustrated in FIG. 6 would be expressed not with a straight line, but with a curve.

Further, for example, in the explanation above, the situation is explained in which the region within the reconstruction region R0 other than the spectrum reconstruction region R1 is determined as the energy integral reconstruction region R2; however, possible embodiments are not limited to this example. For instance, regardless of the shape or the size of the spectrum reconstruction region R1, the determining function 372 may always determine the entirety of the reconstruction region R0 as the energy integral reconstruction region R2. The image of the spectrum reconstruction region R1 may be superimposed so as to hide a corresponding region in the energy integral reconstruction region R2. Alternatively, an image of the spectrum reconstruction region R1 may be superimposed while having a predetermined degree of transparency (while being translucent, or the like).

Further, for example, although FIG. 7A illustrates the example in which the spectrum reconstruction region R1 having a circular shape is determined, possible embodiments are not limited to this example. For instance, even when a set made up of pixels of which the output values corresponding to all the views are each smaller than the threshold value does not have a circular shape but has an odd shape or a shape of which the outline is formed by discontinuous line segments, the determining function 372 is able to determine the set of pixels as a spectrum reconstruction region R1. For example, by implementing a least-squares method or the like, it is possible to transform such a shape of which the outline is formed by discontinuous line segments, into a shape defined by a continuous line (a smooth line). It should be noted, however, that it is desirable for the determining function 372 to determine the spectrum reconstruction region R1 so as to have a circular or oval shape, to achieve an enhanced level of browsability. In this situation, the spectrum reconstruction region R1 may be transformed to have an arbitrary shape such as an inscribed circle of the original shape, a circumscribed circle of the original shape, a circle between the inscribed circle and the circumscribed circle, or the like. The transforming process may be performed so as to automatically transform the original shape into a predetermined shape. Alternatively, a designation of the transformed shape may be received from the operator.

The display controlling function 373 is configured to cause the spectrum reconstruction image and the energy integral reconstruction image to be displayed mutually at the same time. For example, the display controlling function 373 causes the spectrum reconstruction image to be displayed while being superimposed over the energy integral reconstruction image. More specifically, the display controlling function 373 causes the display 32 to display the spectrum reconstruction image so as to be superimposed into a corresponding position of the energy integral reconstruction image. The display controlling function 373 is an example of a display controlling unit.

Further, the display controlling function 373 is configured to cause the spectrum reconstruction image and the energy integral reconstruction image to be displayed in such a manner that these two images are distinguishable from each other. For example, by displaying a boundary line at the boundary of the spectrum reconstruction image and the energy integral reconstruction image, the display controlling function 373 displays these two images in a distinguishable manner. Further, for example, by using mutually-different display modes for the spectrum reconstruction image and the energy integral reconstruction image, the display controlling function 373 displays these two images in a distinguishable manner. More specifically, by displaying the spectrum reconstruction image in color and displaying the energy integral reconstruction image in black and white, the display controlling function 373 displays these two images in a distinguishable manner.

Figure 8:
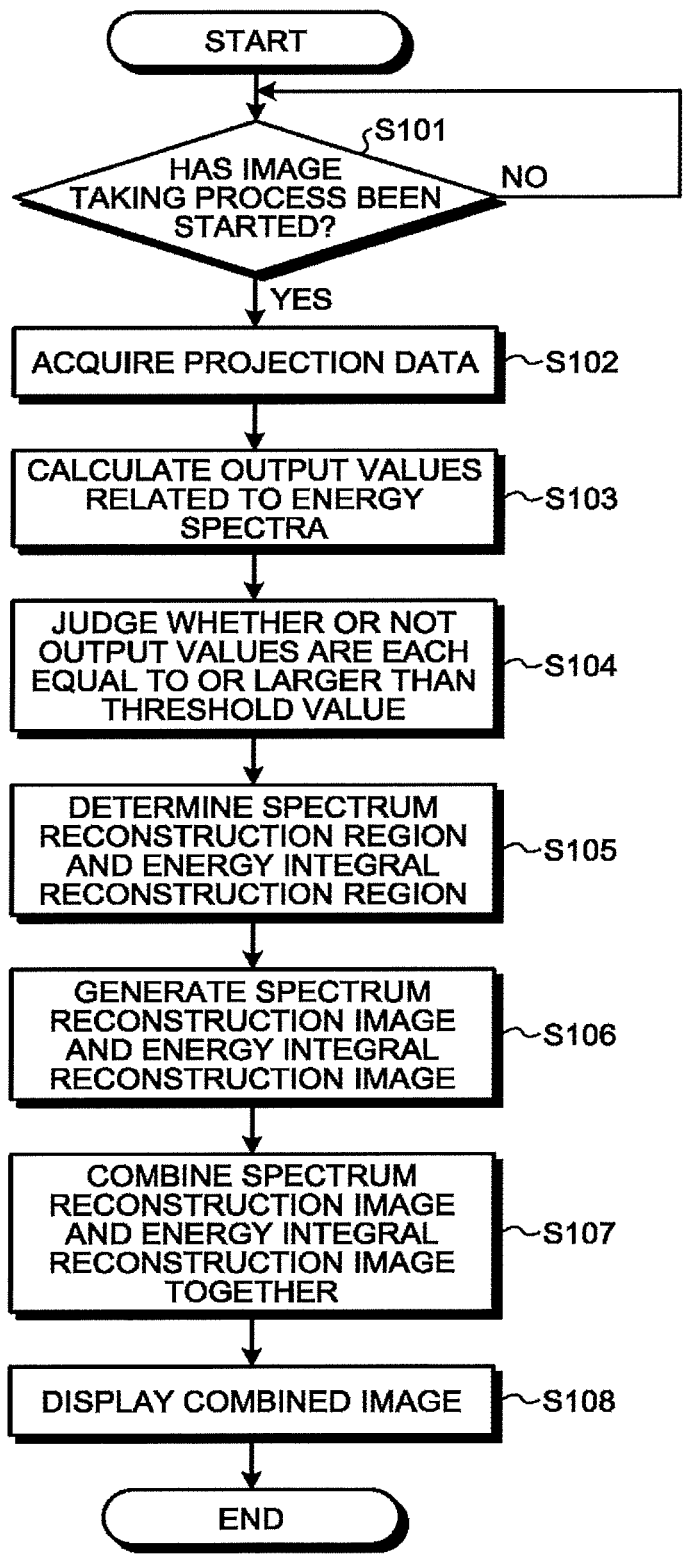
FIG. 8 is a flowchart illustrating a processing procedure performed by the X-ray CT apparatus according to the first embodiment.

FIG. 8 is a flowchart illustrating a processing procedure performed by the X-ray CT apparatus 1 according to the first embodiment. FIG. 8 illustrates the processing procedure to arrange the spectrum reconstruction image and the energy integral reconstruction image to be displayed at the same time as each other. In the present example, FIG. 8 illustrates the processing procedure in a main scan (a main image taking process). In other words, before the processing procedure illustrated in FIG. 8 starts, the process of taking a scanogram (a position determining image) and the process of setting the image taking conditions or the like have already been performed, as necessary.

As illustrated in FIG. 8, at step S101, the processing circuitry 37 judges whether or not an image taking process has been started. For example, when setting of image taking conditions has been completed, the operator inputs an instruction indicating that an image taking process should be started. When the instruction is input by the operator, the processing circuitry 37 starts the image taking process and performs the processes at step S102 and thereafter. When the judgment result at step S101 is in the negative, the processing circuitry 37 does not start the image taking process and remains in a standby state.

When the judgment result at step S101 is in the affirmative, the scan controlling circuitry 33 acquires projection data at step S102. For example, by controlling operations of the X-ray radiation controlling circuitry 11, the gantry driving circuitry 16, the DAS 14, and the couch driving device 21 according to the image taking conditions set by the operator, the scan controlling circuitry 33 causes the data acquiring process to be performed in the gantry 10. After that, the scan controlling circuitry 33 arranges the count results acquired by the DAS 14 to be transmitted to the console 30. The pre-processing circuitry 34 performs the various types of pre-processing processes on the count results received by the console 30, before the count results are stored into the storage 35 as projection data.

At step S103, the judging function 371 calculates output values related to energy spectra. For example, the judging function 371 calculates, for each of the views, the output values in the detection positions, by using the energy spectra corresponding to the detection positions.

At step S104, the judging function 371 judges whether or not the output values are each equal to or larger than the threshold value. For example, for each of the views, the judging function 371 judges whether or not the output value in each of the detection positions is equal to or larger than the threshold value.

At step S105, the determining function 372 determines a spectrum reconstruction region and an energy integral reconstruction region. For example, on the basis of the judgment results obtained by the judging function 371, the determining function 372 judges whether each of the positions (the pixel positions) in the reconstruction region R0 is in the spectrum reconstruction region R1 or the energy integral reconstruction region R2. More specifically, when the output values of all the views (paths) going through a certain position are each smaller than the threshold value, the determining function 372 determines that the position is in the spectrum reconstruction region R1. On the contrary, among all the views going through a certain position, when there is at least one view of which the output values are each equal to or larger than the threshold value, the determining function 372 determines that the position is in the energy integral reconstruction region R2.

At step S106, the image reconstructing circuitry 36 generates a spectrum reconstruction image and an energy integral reconstruction image. For example, by performing a spectrum reconstructing process while using the count results, the image reconstructing circuitry 36 reconstructs X-ray CT image data such as energy discriminatory image data, substance discriminatory image data, monochrome X-ray image data, density image data, effective atomic number image data, and/or the like. Further, for example, by performing an energy integral reconstructing process while using the count results obtained in the photon counting CT procedure, the image reconstructing circuitry 36 calculates energy integral data that is represented by either the sum of the counts of the energy bins or the sum of products of representative values of the energy bins and the counts. After that, the image reconstructing circuitry 36 reconstructs the energy integral reconstruction image, by using the calculated energy integral data.

At step S107, the display controlling function 373 combines together the spectrum reconstruction image and the energy integral reconstruction image. For example, the display controlling function 373 generates a combined image obtained by superimposing the spectrum reconstruction image over the energy integral reconstruction image.

At step S108, the display controlling function 373 causes the combined image to be displayed. For example, the display controlling function 373 causes the display 32 to display the combined image obtained by superimposing the spectrum reconstruction image over the energy integral reconstruction image. After that, the processing circuitry 37 ends the processing procedure illustrated in FIG. 8.

The processing procedure explained with reference to FIG. 8 is merely an example, and possible embodiments are not limited to this example. For instance, although FIG. 8 illustrates the example in which the processes at steps S103 through S105 are performed after the acquisition of the projection data of all the views is completed at step S102, possible embodiments are not limited to this example. For instance, it is acceptable to sequentially perform the processes at steps S103 through S105 every time the projection data of each of the views has been acquired, even though the acquisition of the projection data of all the views has not been completed at step S102. In that situation, the processes are performed in a real-time manner, so that a spectrum reconstruction region is gradually determined as the acquisition of the projection data progresses.

As explained above, in the X-ray CT apparatus 1 according to the first embodiment, the judging function 371 is configured to judge whether or not the output values related to the energy spectra based on the signals output by the detecting elements are each equal to or larger than the threshold value. Further, within the reconstruction region, the determining function 372 is configured to determine the first region on which the spectrum reconstructing process is to be performed and the second region on which the energy integral reconstructing process is to be performed, on the basis of the judgment results obtained by the judging function 371. Further, the image reconstructing circuitry 36 is configured to generate the first image corresponding to the first region by performing the spectrum reconstructing process and to generate the second image corresponding to the second region by performing the energy integral reconstructing process. With these arrangements, the X-ray CT apparatus 1 according to the first embodiment is able to improve the precision level and the processing speed of the image reconstructing processes in the photon counting CT procedure.

For example, the X-ray CT apparatus 1 performs the spectrum reconstructing process on the region in which the output values corresponding to all the views are each smaller than the threshold value. In that region, because there is little impact from the pile-up phenomenon or the like, the X-ray CT apparatus 1 is able to perform the spectrum reconstructing process by using accurate energy spectra. As a result, the X-ray CT apparatus 1 is able to improve the precision level of the image reconstructing processes. Further, in that situation, because the restoration of the energy spectra is easy (or unnecessary), the X-ray CT apparatus 1 is also able to improve the processing speed of the image reconstructing processes.

A First Modification Example of the First Embodiment

In the embodiment above, the example is explained in which, within the reconstruction region, such a region in which the output values corresponding to all the views are each smaller than the threshold value is determined as the spectrum reconstruction region; however, possible embodiments are not limited to this example. For instance, with respect to each of the positions included in the reconstruction region, the determining function 372 may determine the position to be in the spectrum reconstruction region when, among all the views going through the position, the output values corresponding to views in such a quantity that make a half reconstruction process possible are each smaller than the threshold value.

More specifically, among all the views going through each of the positions, when the output value of such a view that correspond to "a half turn+the fan angle" is smaller than the threshold value, the determining function 372 may determine that the position is in the spectrum reconstruction region. In that situation, the image reconstructing circuitry 36 generates a spectrum reconstruction image corresponding to the spectrum reconstruction region by performing a half reconstruction process. With these arrangements, the X-ray CT apparatus 1 is able to provide the spectrum reconstruction image corresponding to a larger area.

A Second Modification Example of the First Embodiment

Further, for example, the determining function 372 may further determine a correctable region (a third region) on which it is possible to perform a spectrum reconstructing process with a correction.

For example, among the views of which the output values are each determined to be equal to or larger than the threshold value, the determining function 372 determines such a position that includes a view with which it is possible to perform a spectrum reconstructing process by correcting the output value, to be in the correctable region. Further, after correcting the output values in the correctable region, the image reconstructing circuitry 36 generates a spectrum reconstruction image corresponding to the correctable region by performing a spectrum reconstructing process.

In this situation, the determining function 372 determines a spectrum reconstruction region, an energy integral reconstruction region, and the correctable region, by using a threshold value Th1 and a threshold value Th2. For example, the threshold values Th1 and Th2 are values satisfying "Th1<Th2".

For example, the determining function 372 determines such a region in which the output values corresponding to all the views are each smaller than the threshold value Th1 as the spectrum reconstruction region. Further, the determining function 372 determines such a region in which the output values corresponding to all the views are each equal to or larger than the threshold value Th1 but smaller than the threshold value Th2 as the correctable region. Furthermore, the determining function 372 determines the remaining region of the reconstruction region as the energy integral reconstruction region.

Subsequently, after performing a correcting process by applying a pile-up correction to the output values in the correctable region, the image reconstructing circuitry 36 generates a spectrum reconstruction image by performing a spectrum reconstructing process. In this situation, because the processes performed on the spectrum reconstruction region and the energy integral reconstruction region are the same as those in the first embodiment, the explanations thereof will be omitted.

In this manner, the determining function 372 is configured to further determine the correctable region on which it is possible to perform the spectrum reconstructing process with the correction. With these arrangements, the X-ray CT apparatus 1 is able to provide the spectrum reconstruction image corresponding to a larger area.

A Third Modification Example of the First Embodiment

Further, for example, the determining function 372 may determine a region that is positioned outside such a view of which the output value is determined to be equal to or larger than the threshold value, as an energy integral reconstruction region.

For example, within the reconstruction region R0, the determining function 372 determines a region positioned outside such a view of which the output value is determined to be equal to or larger than the threshold value, as an energy integral reconstruction region. In one example, when the output value of the position P1 illustrated in FIG. 5 is determined to be equal to or larger than the threshold value, there is a high possibility that the output value of the position P2 positioned on the outside of the position P1 may also be determined to be equal to or larger than the threshold value. For this reason, when the output value of the position P1 is determined to be equal to or larger than the threshold value, the determining function 372 determines the region positioned on the outside and including the position P2 as the energy integral reconstruction region.

With these arrangements, the determining function 372 is able to omit the determining process for such a region of which the output value has a high possibility of being determined to be equal to or larger than the threshold value.

As a result, the X-ray CT apparatus 1 is able to further improve the processing speed in the present embodiment.

A Fourth Modification Example of the First Embodiment

For example, the processes performed in the above embodiment are applicable to a reconstruction processing apparatus that operates in a network.

Figure 9:
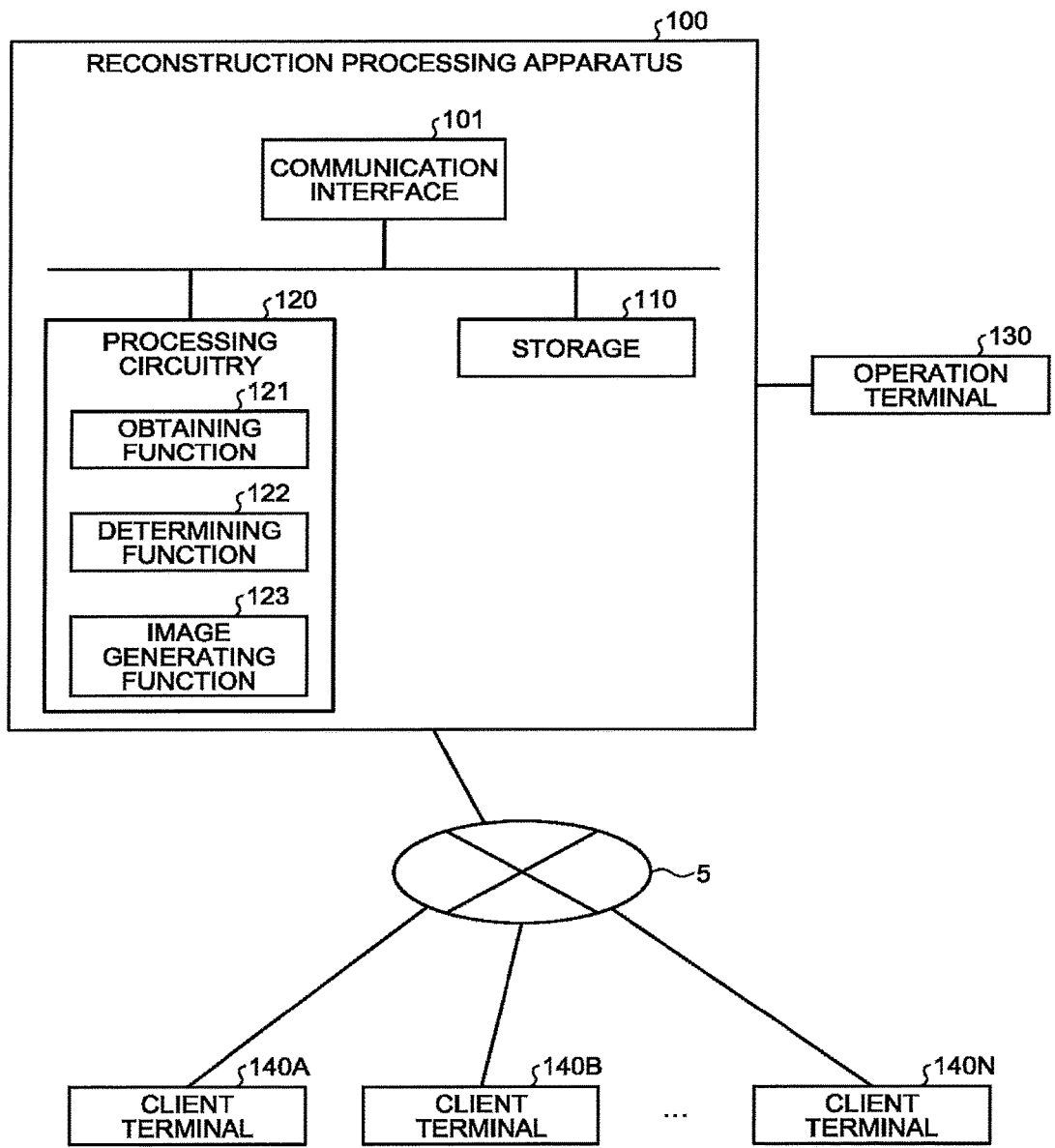
FIG. 9 is a block diagram illustrating an exemplary configuration of a reconstruction processing apparatus according to a modification example of the first embodiment.

FIG. 9 is a block diagram illustrating an exemplary configuration of a reconstruction processing apparatus according to a fourth modification example of the first embodiment. As illustrated in FIG. 9, a reconstruction processing apparatus 100 is, for example, installed in a service center that provides reconstructing processes as an information processing service. The reconstruction processing apparatus 100 is connected to an operation terminal 130. Further, the reconstruction processing apparatus 100 is connected to a plurality of client terminals 140A, 140B, . . . and 140N via a network 5. Alternatively, the reconstruction processing apparatus 100 and the operation terminal 130 may be connected to each other via the network 5. When being referred to without being distinguished from one another, the plurality of client terminals 140A, 140B, and 140N will be referred to as "client terminals 140".

The operation terminal 130 is an information processing terminal used by a person (an operator) who operates the reconstruction processing apparatus 100. For example, the operation terminal 130 includes an input device used for receiving various types of instructions and setting requests from the operator, such as a mouse, a keyboard, a touch panel, and/or the like. Further, the operation terminal 130 includes a display device configured to display an image and to display a GUI used by the operator for inputting the various types of setting requests through the input device. By operating the operation terminal 130, the operator is able to transmit the various types of instructions and setting requests to the reconstruction processing apparatus 100 and to browse information inside the reconstruction processing apparatus 100. Further, the network 5 is an arbitrary communication network such as the Internet, a Wide Area Network (WAN), a Local Area Network (LAN), or the like.

Each of the client terminals 140 is an information processing apparatus having a client function capable of using the information processing service provided by the reconstruction processing apparatus 100. For example, each of the client terminals 140 corresponds to a personal computer, a workstation, a console device included in an X-ray CT apparatus, or the like. A user who uses the information processing service uses the information processing service, by operating any of the client terminals 140. In this situation, the user may be, for example, a medical provider such as a medical doctor or technician working in a medical institution. The client function of the client terminals 140 is recorded, in advance, in the form of a computer-executable program in a storage (a storage device) provided inside each client terminal 140.

The reconstruction processing apparatus 100 includes a communication interface 101, a storage 110, and processing circuitry 120. The communication interface 101, the storage 110, and the processing circuitry 120 are connected together so as to be able to communicate with one another.

For example, the communication interface 101 is a network card or a network adaptor. By connecting to the network 5, the communication interface 101 realizes information communication between the reconstruction processing apparatus 100 and an external apparatus.

The storage 110 is, for example, a Not AND (NAND) flash memory or a Hard Disk Drive (HDD) and is configured to store therein various types of programs used for displaying medical image data and a GUI, as well as information used by the programs.

The processing circuitry 120 is an electronic device (a processor) configured to control the entire processes performed by the reconstruction processing apparatus 100. The processing circuitry 120 executes an obtaining function 121, a determining function 122, and an image generating function 123. The processing functions executed by the processing circuitry 120 are, for example, recorded in the storage 110 in the form of computer-executable programs. By reading and executing the programs, the processing circuitry 120 realizes the functions corresponding to the read programs. The obtaining function 121 is an example of an obtaining unit. The determining function 122 is an example of the determining unit. The image generating function 123 is an example of the image generating unit.

For example, by operating any of the client terminals 140, the user inputs an instruction indicating that projection data be transmitted to (uploaded into) the reconstruction processing apparatus 100 provided at the service center. When the instruction is input, the client terminal 140 transmits the projection data to the reconstruction processing apparatus 100. In this situation, the projection data is data acquired by an X-ray CT apparatus capable of executing a photon counting CT procedure. The projection data is data at a stage where the various types of processes performed by the pre-processing circuitry 34 illustrated in FIG. 1 have been completed. In the present example, the situation in which the projection data is transmitted to the reconstruction processing apparatus 100 will be explained; however, possible embodiments are not limited to this example.

Further, in the reconstruction processing apparatus 100, the obtaining function 121 is configured to obtain the output values related to the energy spectra based on the signals output from the plurality of detecting elements included in a photon counting detector that outputs signals in response to X-rays becoming incident thereto after having passed through a patient. In other words, the obtaining function 121 receives the projection data transmitted thereto from the client terminal 140. The projection data contains information about the energy spectra based on the signals output by the detecting elements in correspondence with the views. The obtaining function 121 calculates the output values for each of the views, by using the energy spectra corresponding to the views. As a result, the obtaining function 121 obtains the output values related to the energy spectra.

Further, within the reconstruction region, the determining function 122 is configured to determine, on the basis of the output values, the first region on which the spectrum reconstructing process is to be performed and the second region on which the energy integral reconstructing process is to be performed. For example, the determining function 122 is capable of performing the same processes as those performed by the judging function 371 and the determining function 372 illustrated in FIG. 1. More specifically, the determining function 122 is configured to determine, within the reconstruction region, the spectrum reconstruction region (the first region) on which the spectrum reconstructing process is to be performed and the energy integral reconstruction region (the second region) on which the energy integral reconstructing process is to be performed, by performing the same processes as those performed by the judging function 371 and the determining function 372.

Further, the image generating function 123 is configured to generate images on the basis of the determination made by the determining function 122. For example, the image generating function 123 is capable of performing the same processes as those performed by the image reconstructing circuitry 36 illustrated in FIG. 1. More specifically, for the spectrum reconstruction region R1, the image generating function 123 generates a spectrum reconstruction image, by performing a spectrum reconstructing process. Further, for the energy integral reconstruction region R2, the image generating function 123 generates an energy integral reconstruction image by performing an energy integral reconstructing process.

Further, the reconstruction processing apparatus 100 is configured to output the images generated by the image generating function 123. For example, the reconstruction processing apparatus 100 transmits the images generated by the image generating function 123 to the client terminal 140 (or causes the client terminal 140 to download the images). As a result, the reconstruction processing apparatus 100 is able to improve the precision level and the processing speed of the image reconstructing processes in the photon counting CT procedure. Consequently, the user of the client terminal 140 is able, for example, to browse the images of which the precision levels of the image reconstructing processes have been improved.

Further, for example, even when using projection data acquired by an X-ray CT apparatus that does not have the reconstructing function or when using projection data acquired by an X-ray CT apparatus that has only a simple reconstructing function, the reconstruction processing apparatus 100 is able to improve the precision level and the processing speed of the image reconstructing processes in the photon counting CT procedure. In other words, when the reconstruction processing apparatus 100 is used, for example, it is possible to simplify the configurations of X-ray CT apparatuses that are installed in facilities such as medical institutions.

In other words, it is possible to provide the processes in the embodiment described above as a reconstruction processing method, by providing the reconstruction processing apparatus 100 installed in the network therewith. The reconstruction processing method includes a process performed by the reconstruction processing apparatus 100 to obtain the output values related to the energy spectra based on the signals output from the plurality of detecting elements of a photon counting detector that outputs signals in correspondence with X-rays becoming incident thereto after having passed through a patient. Further, the reconstruction processing method includes a process performed by the reconstruction processing apparatus 100 to determine, within the reconstruction region, the first region on which the spectrum reconstructing process is to be performed and the second region on which the energy integral reconstructing process is to be performed, on the basis of the output values. Further, the reconstruction processing method includes a process performed by the reconstruction processing apparatus 100 to generate an image on the basis of the determination.

Second Embodiment

Next, an X-ray CT apparatus according to another embodiment will be explained, with reference to the accompanying drawings.

The X-ray CT apparatus described in the embodiment below is an apparatus capable of executing a photon counting CT procedure. In other words, the X-ray CT apparatus described in the embodiment below is an apparatus capable of reconstructing X-ray CT image data having a high S/N ratio, by counting X-rays that have passed through a patient while using, not a conventional integral detector (that implements a current mode measuring method), but a detector that implements a photon counting method. Further, the contents of each of the embodiments are, in principle, similarly applicable to any other embodiment.

Figure 10:
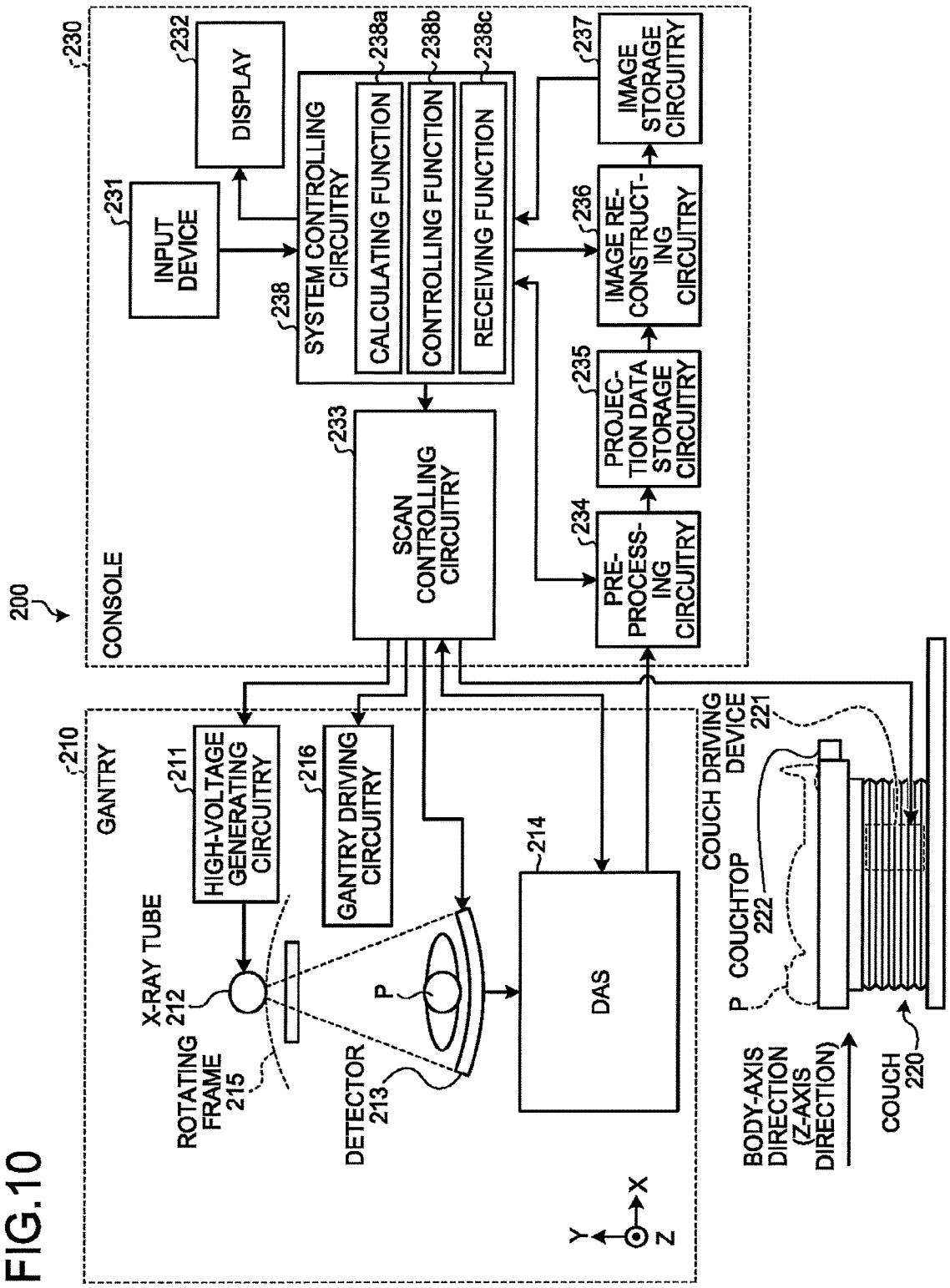
FIG. 10 is a diagram illustrating an exemplary configuration of an X-ray CT apparatus according to a second embodiment.

FIG. 10 is a block diagram illustrating an exemplary configuration of an X-ray CT apparatus according to a second embodiment. As illustrated in FIG. 10, an X-ray CT apparatus 200 according to the second embodiment includes a gantry 210, a couch 220, and a console 230.

The gantry 210 is a device configured to radiate X-rays onto the patient P and to acquire data related to X-rays that have passed through the patient P. The gantry 210 includes: high-voltage generating circuitry 211, an X-ray tube 212, a detector 213, DAS 214, a rotating frame 215, and gantry driving circuitry 216. Further, as illustrated in FIG. 10, by the gantry 210, an orthogonal coordinate system structured with an X-axis, a Y-axis, and a Z-axis is defined. In other words, the X-axis expresses the horizontal direction, while the Y-axis expresses the vertical direction, and the Z-axis expresses the axial direction of the rotation center of the rotating frame 215 observed while the gantry 210 is not tilted.

The rotating frame 215 is an annular frame configured to support the X-ray tube 212 and the detector 213 so as to oppose each other while the patient P is interposed therebetween and configured to be rotated by the gantry driving circuitry 216 (explained later) at a high speed on a circular orbit centered on the patient P.

The X-ray tube 212 is a vacuum tube configured to radiate an X-ray beam onto the patient P by using a high voltage supplied thereto by the high-voltage generating circuitry 211 (explained later). The X-ray tube 212 is configured to radiate the X-ray beam onto the patient P, as the rotating frame 215 rotates.

The high-voltage generating circuitry 211 is an electrical circuit having a function of supplying the high voltage to the X-ray tube 212. The X-ray tube 212 is configured to generate the X-rays by using the high voltage supplied thereto from the high-voltage generating circuitry 211. In other words, the high-voltage generating circuitry 211 adjusts the dose of X-rays to be radiated onto the patient P, by adjusting the X-ray tube voltage and/or the X-ray tube current supplied to the X-ray tube 212. The high-voltage generating circuitry 211 is controlled by scan controlling circuitry 233 under control of system controlling circuitry 238.

The gantry driving circuitry 216 is an electrical circuit having a function of causing the X-ray tube 212 and the detector 213 to revolve on a circular orbit centered on the patient P, by driving the rotating frame 215 to rotate. The gantry driving circuitry 216 is controlled by the scan controlling circuitry 233, under the control of the system controlling circuitry 238.

The detector 213 is a detector of a photon counting type (hereinafter, "photon counting detector") and includes a plurality of X-ray detecting elements (hereinafter "sensors" or simply "detecting elements") used for counting light beams derived from the X-rays that have passed through the patient P. In one example, the X-ray detecting elements included in the detector 213 according to the second embodiment are each a planar detector of an indirect conversion type structured with a scintillator and an optical sensor. In the present example, the optical sensor is a Silicon PhotoMultiplier (SiPM), for example. Each of the X-ray detecting elements included in the detector 213 is configured to output an electrical signal (a pulse) corresponding to an X-ray photon that has become incident thereto. The electrical signals output by the X-ray detecting elements may be referred to as detection signals. In other words, the detector 213 includes the plurality of detecting elements that are each configured to detect radiation and to output a detection signal. The peak value of each of the electrical signals (the pulses) has a correlation with an energy value of the X-ray photon. Alternatively, the detector 213 may be a planar detector of a direct conversion type.

The DAS 214 is an electrical circuit having a function of acquiring a count result, which is a result of a counting process using the detection signals from the detector 213. The DAS 214 is configured to count photons (X-ray photons) derived from the X-rays that are radiated from the X-ray tube 212 and have passed through the patient P and to acquire, as the count result, a result of discriminating energy levels of the counted photons. After that, the DAS 214 transmits the count result to the console 230. The DAS 214 may be referred to as a Data Acquisition System (DAS). The DAS 214 is sometimes called data acquiring circuitry.

The couch 220 is a device on which the patient P is placed and includes a couchtop 222 and a couch driving device 221. The couchtop 222 is a board on which the patient P is placed. The couch driving device 221 is configured to move the patient P into the rotating frame 215 by moving the couchtop 222 in the Z-axis direction. The couch driving device 221 is also capable of moving the couchtop 222 in the X-axis direction.

For example, the gantry 210 performs a helical scan by which the patient P is helically scanned by causing the rotating frame 215 to rotate while the couchtop 222 is being moved. In another example, the gantry 210 performs a conventional scan by which the patient P is scanned on a circular orbit by causing the rotating frame 215 to rotate, while the position of the patient P is being fixed after the couchtop 222 is moved. In the embodiment described below, an example will be explained in which the relative position between the gantry 210 and the couchtop 222 can be changed by controlling the couchtop 222; however, possible embodiments are not limited to this example. For instance, when the gantry 210 is self-propelled, the relative position between the gantry 210 and the couchtop 222 may be changed by controlling the self-propelled movement of the gantry 210.

The console 230 is a device configured to receive operations performed by the operator on the X-ray CT apparatus 1 and also configured to reconstruct X-ray CT image data by using the count result acquired by the gantry 210. As illustrated in FIG. 10, the console 230 includes an input device 231, a display 232, the scan controlling circuitry 233, pre-processing circuitry 234, projection data storage circuitry 235, image reconstructing circuitry 236, image storage circuitry 237, and the system controlling circuitry 238.

The input device 231 includes a mouse, a keyboard, and/or the like used by the operator of the X-ray CT apparatus to input various types of instructions and various types of settings. The input device 231 is configured to transfer information about the instructions and the settings received from the operator to the system controlling circuitry 238. For example, the input device 231 receives, from the operator, a reconstruction condition used when the X-ray CT image data is reconstructed, an image processing condition applied to the X-ray CT image data, and the like. Further, for example, the input device 231 receives, from the operator, an instruction indicating that a calibration process should be performed on the X-ray detecting elements. Further, via the system controlling circuitry 238, the input device 231 instructs the scan controlling circuitry 233 to perform the X-ray CT image data reconstructing process or the calibration process.

The display 232 is a monitor referenced by the operator. Under the control of the system controlling circuitry 238, the display 232 is configured to display the X-ray CT image data for the operator and to display a Graphical User Interface (GUI) used for receiving the various types of instructions and the various types of settings from the operator via the input device 231.

Figure 11:
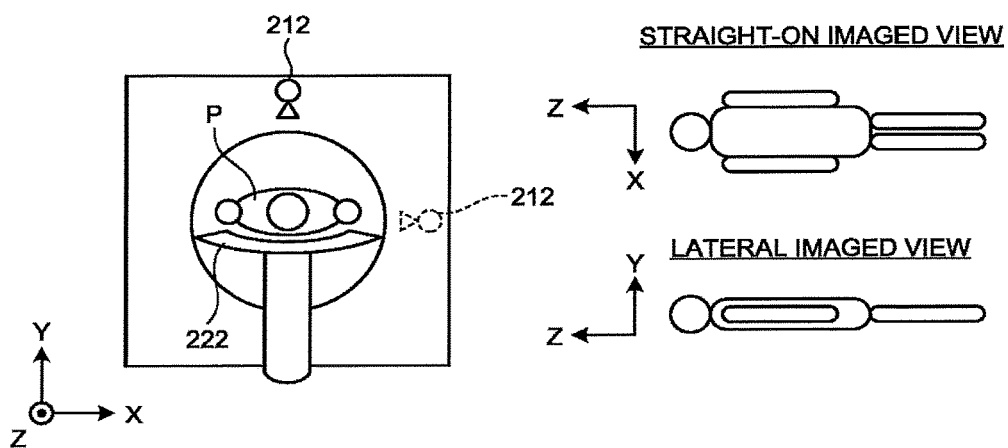
FIG. 11 is a drawing for explaining a two-dimensional scanogram taking process.

The scan controlling circuitry 233 is an electrical circuit having a function of controlling the count result acquiring process performed by the gantry 210, by controlling operations of the high-voltage generating circuitry 211, the detector 213, the gantry driving circuitry 216, the DAS 214, and the couch driving device 221, under the control of the system controlling circuitry 238 (explained later). The scan controlling circuitry 233 is a processor, for example, and by reading and executing the programs, the scan controlling circuitry 233 is configured to realize the functions corresponding to the read programs. More specifically, the scan controlling circuitry 233 is configured to control an image taking process to acquire a position determining image (a scanogram image) and a projection data acquiring process in a main image taking process (a scan) to acquire an image used in a diagnosis process. With the X-ray CT apparatus according to the second embodiment, an example will be explained in which a two-dimensional scanogram image (a two-dimensional scanogram) is taken. FIG. 11 is a drawing for explaining a two-dimensional scanogram taking process.

The left section of FIG. 11 is a drawing of a view of the CT apparatus from the front (the couch 220 side). As illustrated in the left section of FIG. 11, the patient P is placed on the couchtop 222 of the couch 220. In this situation, for example, when an image taking process is performed while the X-ray tube 212 is in the 0-degree position (i.e., a position in the positive direction on the Y-axis in the left section of FIG. 11, which is in a straight-on direction with respect to the patient P), the image taking process is performed from the straight-on side of the patient P so as to obtain a two-dimensional scanogram illustrated in the upper right section of FIG. 11. In that situation, the scan controlling circuitry 233 takes the two-dimensional scanogram by continuously taking images by moving the couchtop 222 at a constant speed, while the X-ray tube 212 is fixed in the 0-degree position. Alternatively, the scan controlling circuitry 233 may take a two-dimensional scanogram by intermittently moving the couchtop 222 and intermittently taking images repeatedly in synchronization with the moving of the couchtop 222, while the X-ray tube 212 is fixed in the 0-degree position.

In another example, the scan controlling circuitry 233 is also capable of taking a position determining image, not only from the straight-on direction of the patient, but also from any arbitrary direction (e.g., a lateral direction). For example, when an image taking process is performed while the X-ray tube 212 is in the 90-degree position (i.e., a position in the positive direction on the X-axis in the left section of FIG. 11, which is in a lateral direction with respect to the patient P), the image taking process is performed from the lateral side of the patient P so as to obtain a two-dimensional scanogram illustrated in the lower right section of FIG. 11. The image taking process may be performed while the X-ray tube 212 is being arranged in arbitrary multiple positions, when necessary.

The pre-processing circuitry 234 is an electrical circuit having a function of generating projection data corresponding to each of the energy discriminatory zones by performing a logarithmic converting process as well as correcting processes such as an offset correcting process, a sensitivity correcting process, a beam hardening correcting process, and the like, on the count results transmitted thereto from the DAS 214. Further, the pre-processing circuitry 234 is also configured to output the count results transmitted thereto from the DAS 214, to the system controlling circuitry 238 in response to an instruction from the system controlling circuitry 238. The pre-processing circuitry 234 is a processor, for example, and by reading and executing the programs, the pre-processing circuitry 234 is configured to realize the functions corresponding to the read programs.

The projection data storage circuitry 235 is configured by using a Not AND (NAND) flash memory or a Hard Disk Drive (HDD), for example, and is configured to store therein the projection data generated by the pre-processing circuitry 234. In other words, the projection data storage circuitry 235 is configured to store therein the projection data used for reconstructing the X-ray CT image data. The image storage circuitry 237 is configured by using a NAND flash memory or an HDD, for example, and is configured to store therein various types of image data.

The image reconstructing circuitry 236 is an electrical circuit having a function of reconstructing the CT image on the basis of the detection signals from the detector 213. The image reconstructing circuitry 236 is a processor, for example, and by reading and executing the programs, the image reconstructing circuitry 236 is configured to realize functions corresponding to the read programs. In other words, the image reconstructing circuitry 236 is configured to reconstruct the X-ray CT image data by performing, for example, a back projection process on the projection data stored in the projection data storage circuitry 235. Examples of the back projection process include a back projection process using a Filtered Back Projection (FBP) method. Alternatively, the image reconstructing circuitry 236 may perform the reconstructing process by using a successive approximation method, for example. Further, the image reconstructing circuitry 236 is configured to generate image data by performing various types of image processing processes on the X-ray CT image data. The image reconstructing circuitry 236 stores the reconstructed X-ray CT image data and the image data generated by performing the various types of image processing processes, into the image storage circuitry 237.

In the present example, the projection data generated from the count results obtained in the photon counting CT procedure includes information about the energy levels of the X-rays that were attenuated as a result of having passed through the patient P. For this reason, the image reconstructing circuitry 236 is able to reconstruct, for example, X-ray CT image data rendering specific energy component. Further, the image reconstructing circuitry 236 is capable of reconstructing, for example, X-ray CT image data of each of a plurality of energy components.

Further, for example, the image reconstructing circuitry 236 is capable of generating image data in which a plurality of pieces of X-ray CT image data are superimposed on one another, by assigning a color tone corresponding to an energy component to each of the pixels in the X-ray CT image data representing various energy components, so as to color-code the pixels in accordance with the energy components. Further, for example, by using k-absorption edges that are each unique to a substance, the image reconstructing circuitry 236 is capable of generating image data that makes it possible to identify various substances. Examples of other types of image data that can be generated by the image reconstructing circuitry 236 include monochrome X-ray image data, density image data, and effective atomic number image data.

The system controlling circuitry 238 is an electrical circuit having a function of exercising overall control of the X-ray CT apparatus by controlling operations of the gantry 210, the couch 220, and the console 230. More specifically, the system controlling circuitry 238 is configured to control a CT scan performed by the gantry 210, by controlling the scan controlling circuitry 233. Also, the system controlling circuitry 238 is configured to control the image reconstructing process and the image generating process performed by the console 230, by controlling the pre-processing circuitry 234 and the image reconstructing circuitry 236. Further, the system controlling circuitry 238 is configured to exercise control so that the display 232 displays any of the various types of image data stored in the image storage circuitry 237.

Further, as illustrated in FIG. 10, the system controlling circuitry 238 according to the second embodiment is configured to execute a calculating function 238a, a controlling function 238b, and a receiving function 238c. In this situation, for example, processing functions executed by the constituent elements of the system controlling circuitry 238 illustrated in FIG. 10, namely the functions such as the calculating function 238a, the controlling function 238b, and the receiving function 238c are recorded in the system controlling circuitry 238 in the form of computer-executable programs. The system controlling circuitry 238 is a processor, for example, and by reading and executing the programs, the system controlling circuitry 238 is configured to realize the functions corresponding to the read programs. In other words, the system controlling circuitry 238 that has read the programs has the functions illustrated within the system controlling circuitry 238 in FIG. 10. The calculating function 238a is an example of a calculating unit. The controlling function 238b is an example of a controlling unit. The receiving function 238c is an example of a receiving unit. Details of the calculating function 238a, the controlling function 238b, and the receiving function 238c will be explained later.

An overall configuration of the X-ray CT apparatus according to the second embodiment has thus been explained. The X-ray CT apparatus according to the second embodiment structured as described above is configured to reconstruct the X-ray CT image data by using the detector implementing a photon counting method.

Figure 12:
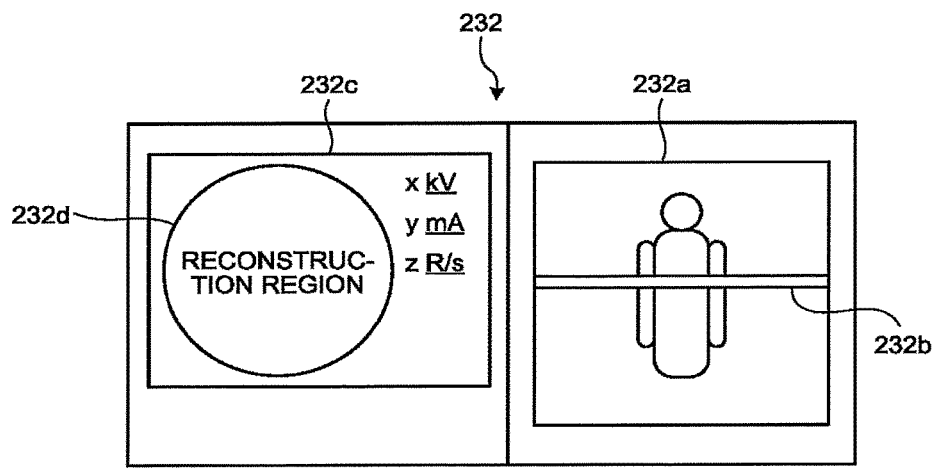
FIG. 12 is a drawing for explaining an image taking condition setting process for a main image taking process.

In this situation, for example, the X-ray CT apparatus performs a main image taking process under the image taking conditions set by using the scanogram images. FIG. 12 is a drawing for explaining an image taking condition setting process for the main image taking process. FIG. 12 illustrates an example in which the display 232 is divided into two sections represented by a display region 232a and a display region 232c. In the display region 232a in FIG. 12, a two-dimensional scanogram taken while the X-ray tube 212 is in the 0-degree position is displayed. In the present example, when the operator selects a cross-sectional plane of interest 232b in the two-dimensional scanogram, the X-ray CT apparatus displays, in the display region 232c, a reconstruction region 232d representing a scan Field of View (FOV) and scan condition parameters. In the example in FIG. 12, the X-ray CT apparatus displays, as the scan condition parameters, an X-ray tube voltage x (kV), an X-ray tube current y (mA), and a rotation speed z (R/s).

In relation to this, during the photon counting CT procedure, the X-ray dose is measured by counting the quantity of photons. The larger the quantity of photons per unit time period is, the stronger the X-rays are. Further, individual photons have mutually-different energy levels; however, during the photon counting CT procedure, it is possible to obtain information about energy components of the X-rays, by measuring the energy of the photons. In other words, in the photon counting CT procedure, it is possible to express, in an image, the data acquired by radiating X-rays while using one type of X-ray tube voltage, in such a manner that the data is divided according to the plurality of energy components. For example, in the photon counting CT procedure, such image data is obtained with which it is possible to identify substances by using differences in the k-absorption edges thereof.

In this situation, the absorption amount of X-rays is larger in the center part of the patient, whereas the quantity of X-ray photons that become incident to the detector is smaller. For this reason, because the energy spectrum of the projection data derived from the passing through the center part of the patient P is accurate, it is possible to obtain a reconstruction image in which the substances are discriminated accurately. In contrast, in perimeter parts of the patient or sites having lower levels X-ray absorption, because the quantity of X-ray photons that become incident to the detector is larger, the phenomenon called "pile up" may occur in some situations. The "pile up" is a phenomenon in which, when the detector is unable to count the photons in due time while the count rate is high, some of the photons fail to be counted. When the energy spectrum is inaccurate in this manner, with respect to the projection data derived from the passing through the perimeter part of the patient or through the sites having lower levels of X-ray absorption, it is impossible to obtain a reconstruction image in which the substances are discriminated accurately.

Further, when the acquired projection data includes projection data of which the energy spectrum is inaccurate, an image will be reconstructed by using only the projection data in such a region where the energy spectrum is accurate. However, in some situations, an image reconstructed after an image taking process may not include the region the user wishes to view. In those situations, it may be necessary to perform the image taking process again or it may be impossible to perform a diagnosis process accurately.

To cope with these situations, for the purpose of making it possible for the operator to understand a spectrum reconstruction possible region prior to the main scan, the X-ray CT apparatus according to the second embodiment is configured to perform a process of speculating the spectrum reconstruction possible region. For example, the X-ray CT apparatus calculates output values related to energy spectra from an image of a patient obtained by scanning the patient with X-rays. After that, the X-ray CT apparatus speculates the spectrum reconstruction possible region corresponding to the patient on the basis of the output values related to the energy spectra and causes the display 232 to display the spectrum reconstruction possible region. In the following sections, operations in the process of speculating the spectrum reconstruction possible region according to the second embodiment will be explained in detail, with reference to FIGS. 13 to 17. FIGS. 13 to 17 are drawings for explaining the second embodiment. The following explanation is based on the assumption that the cross-sectional plane of interest 232b illustrated in FIG. 12 has been selected in the two-dimensional scanogram.

The calculating function 238a calculates the output values related to the energy spectra from the image of the patient obtained by scanning the patient with X-rays. In other words, the calculating function 238a calculates the output values related to the energy spectra from an imaging planning-purpose image obtained by imaging the patient by using the X-rays. For example, the calculating function 238a issues an instruction to the pre-processing circuitry 234 and obtains a two-dimensional scanogram from the pre-processing circuitry 234. In this situation, the calculating function 238a obtains, as the image, the two-dimensional scanogram taken from at least one direction. For example, the calculating function 238a obtains a two-dimensional scanogram taken while the X-ray tube 212 is in the 0-degree position and another two-dimensional scanogram taken while the X-ray tube 212 is in the 90-degree position. Alternatively, the calculating function 238a may obtain a two-dimensional scanogram taken from one direction. For example, the calculating function 238a may obtain a two-dimensional scanogram taken while the X-ray tube 212 is in the 0-degree position. Alternatively, the calculating function 238a may obtain a two-dimensional scanogram taken while the X-ray tube 212 is in the 90-degree position. Further, the calculating function 238a may obtain a two-dimensional scanogram taken while the X-ray tube 212 is in an arbitrary position. In this situation, the two-dimensional scanogram is an example of the imaging planning-purpose image.

Figure 13:
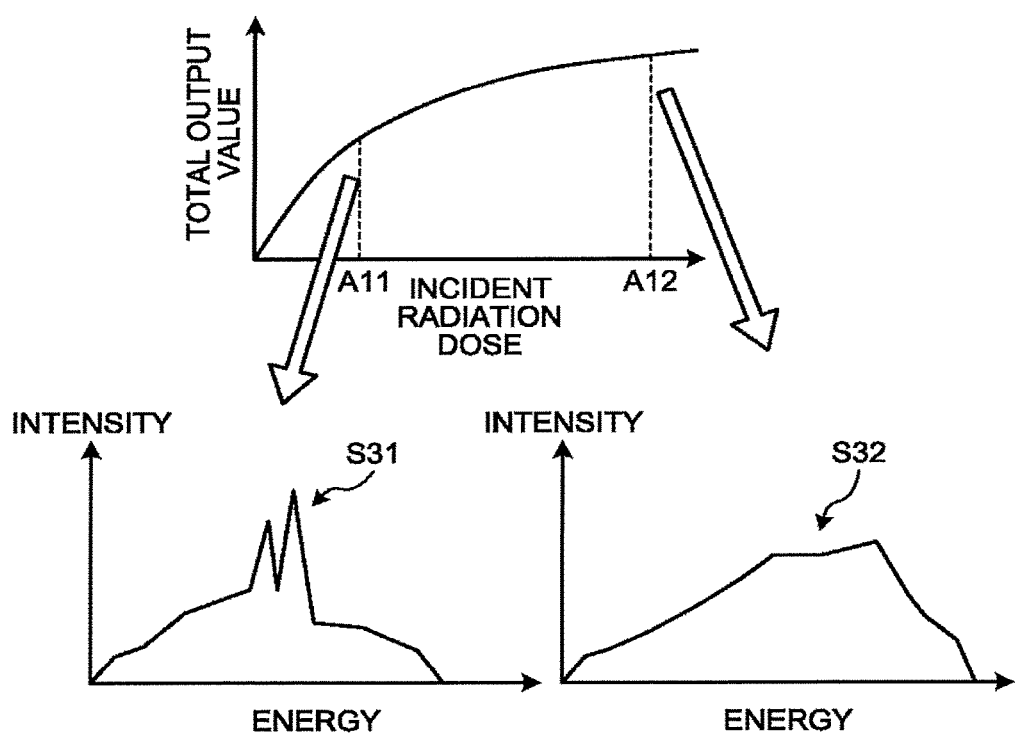
FIG. 13 is a drawing for explaining the second embodiment.

Subsequently, the calculating function 238a calculates the output values in the image for each of the views. For example, the calculating function 238a calculates the output values related to the energy spectra from the two-dimensional scanogram. The top section of FIG. 13 illustrates output values corresponding to incident radiation doses. In this situation, when the incident radiation dose illustrated in the top section of FIG. 13 is A11, for example, an X-ray spectrum S31 illustrated in the bottom left section of FIG. 13 is obtained. Further, when the incident radiation dose illustrated in the top section of FIG. 13 is A12, for example, an X-ray spectrum S32 illustrated in the bottom right section of FIG. 13 is obtained. The calculating function 238a calculates, for each of the views, the output values in the image from the X-ray spectra. In this situation, the scan conditions that are used during the two-dimensional scanogram taking process may be set with a lower X-ray radiation dose than that in the scan conditions used for the main scan. For this reason, the calculating function 238a estimates X-ray spectra under the scan conditions for the main scan, by using the scan conditions and the X-ray spectra from the two-dimensional scanogram taking process and further calculates the output values. For example, on the basis of the two-dimensional scanogram taken while the X-ray tube 212 is in the 0-degree position, the calculating function 238a estimates X-ray spectra corresponding to the X-ray tube 212 being in the 0-degree position under the scan conditions for the main scan and further calculates the output values. Also, on the basis of the two-dimensional scanogram taken while the X-ray tube 212 is in the 90-degree position, the calculating function 238a estimates X-ray spectra corresponding to the X-ray tube 212 being in the 90-degree position under the scan conditions for the main scan and further calculates the output values.

In this situation, the output values are defined as below. In the following sections, for the sake of convenience in the explanation, an example will be explained in which the output values are calculated while the X-ray tube voltage in the scan conditions for the main scan is set to 120 kVp, while the counts of the energy bins are expressed as Ci (where i=1 keV to 120 keV).

For example, the calculating function 238a calculates a total output value of the counts of the energy bins, as the output value. In that situation, the output value can be expressed with Expression (1) presented below.

$$\Sigma C_i (i=1 \text{ to } 20 \text{ keV}) \quad (1)$$

In another example, the calculating function 238a may calculate a pile-up count value of the counts of the energy bins, as the output value. In that situation, the output value can be expressed with Expression (2) presented below.

$$\Sigma C_i (i>120 \text{ keV}) \quad (2)$$

In yet another example, the calculating function 238a may calculate an energy integral value obtained from count values and representative values of the energy bins, as the output value. In that situation, when the median of each of the energy bins is expressed as Ei, for example, the output value can be expressed with Expression (3) presented below.

$$\Sigma (C_i \times E_i)(i=1 \text{ to } 120 \text{ keV}) \quad (3)$$

In yet another example, the calculating function 238a may calculate a pile-up energy integral value of representative values of the energy bins having a pile up, as the output value. In that situation, for example, when the median of each of the energy bins is expressed as Ei, the output value can be expressed with Expression (4) presented below.

$$\Sigma (C_i \times E_i)(i>120 \text{ keV}) \quad (4)$$

Figure 14:
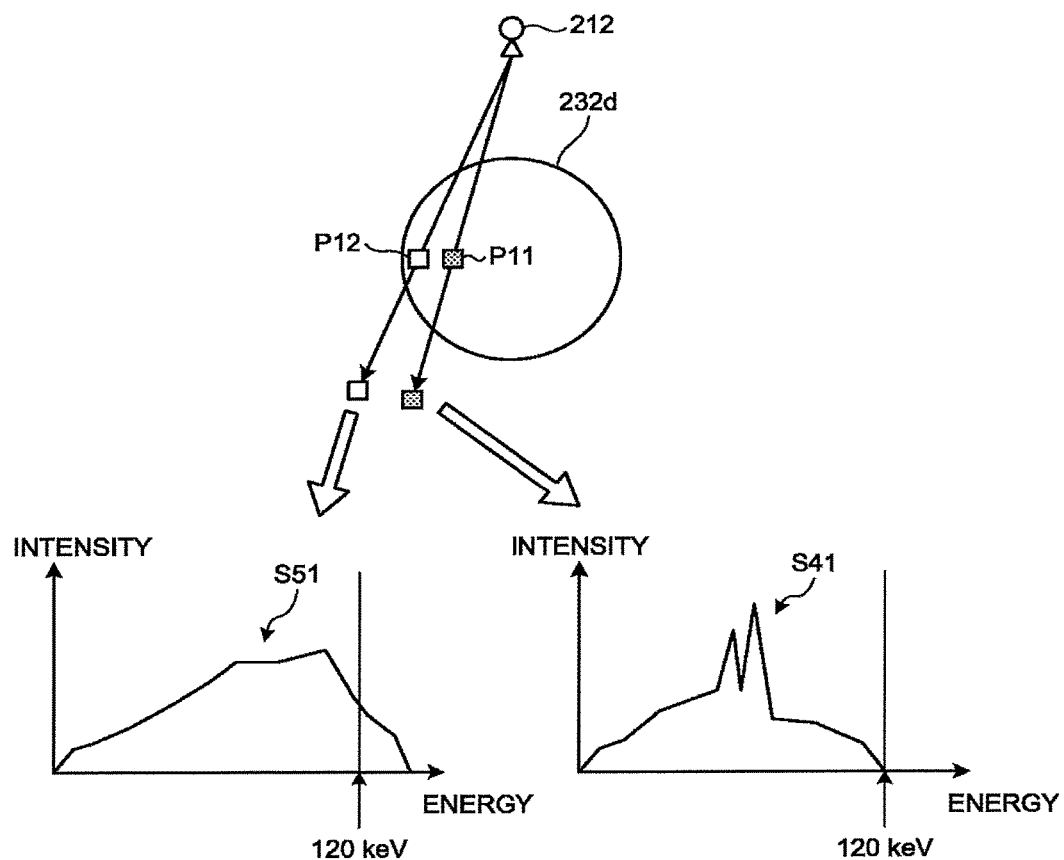
FIG. 14 is another drawing for explaining the second embodiment.

An example of the output value calculating process performed by the calculating function 238a will be explained with reference to FIG. 14. With reference to FIG. 14, an example will be explained in which, while using the two-dimensional scanogram taken while the X-ray tube 212 is in the 0-degree position, output values in a position P11 and a position P12 within the reconstruction region 232d are calculated. The position P12 corresponds to a pixel in a perimeter part of the patient, whereas the position P11 corresponds to a pixel in a center part of the patient that is positioned substantially in the middle of the perimeter part of the patient and the center of the patient.

As illustrated in FIG. 14, the calculating function 238a obtains an X-ray spectrum S41 in the position P11 and obtains an X-ray spectrum S51 in the position P12. Because the X-ray absorption amount is larger in the center part of the patient, the X-ray spectrum S41 in the position P11 corresponding to the center part of the patient does not include energy counts exceeding 120 keV. Further, because the X-ray absorption amount is smaller in the perimeter part of the patient, the X-ray spectrum S51 in the position P12 corresponding to the perimeter part of the patient includes energy counts exceeding 120 keV. In other words, in the position P12, there should theoretically be no X-ray photon having an energy level exceeding 120 keV; however due to the pile-up phenomenon, energy counts exceeding 120 keV are counted in a pseudo manner.

After that, the calculating function 238a calculates, for each of the views, the output values in the image from the obtained X-ray spectra. Although the example is explained with reference to FIG. 14, in which the output values are calculated by obtaining the X-ray spectra only in the position P11 and the position P12, the calculating function 238a actually calculates the output values by obtaining the X-ray spectra in all the positions within the reconstruction region 232d.

Figure 15:
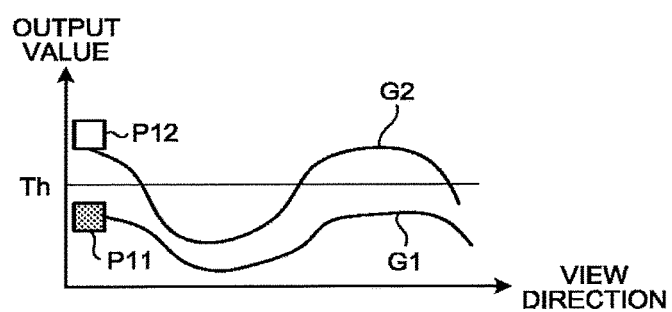
FIG. 15 is yet another drawing for explaining the second embodiment.

Further, on the basis of the calculated output values corresponding to each of images, the calculating function 238a calculates the output values corresponding to all the views. In this situation, for example, when having obtained the two-dimensional scanogram taken while the X-ray tube 212 is in the 0-degree position and the two-dimensional scanogram taken while the X-ray tube 212 is in the 90-degree position, the calculating function 238a calculates output values corresponding to the X-ray tube 212 being in the 0-degree position and output values corresponding to the X-ray tube 212 being in the 90-degree position, on the basis of the obtained two-dimensional scanograms. Further, by utilizing a notion that an axial plane of a human body can be approximated to an oval shape, the calculating function 238a estimates output values other than those corresponding to the X-ray tube 212 being in the 0-degree position and the X-ray tube 212 being in the 90-degree position, on the basis of the obtained two-dimensional scanograms. The vertical axis in FIG. 15 expresses the output values, whereas the horizontal axis in FIG. 15 expresses the view direction. FIG. 15 illustrates the output values corresponding to all the views calculated with respect to the position 211 and the position P12 illustrated in FIG. 14.

For example, as illustrated in FIG. 15, by utilizing the notion that human bodies have an oval shape, the calculating function 238a estimates the output values in the views other than those in the obtained two-dimensional scanograms and further plots the estimated output values in the other views in the view direction. More specifically, the calculating function 238a generates a chart G1 indicating the output values corresponding to all the views with respect to the position 211 and generates a chart G2 indicating the output values corresponding to all the views with respect to the position 212. In this situation, the calculating function 238a uses count rate values (output values per unit time period) or pile-up overage values (pile-up count values per unit time period) as the output values. Further, the calculating function 238a may adjust the estimated output values in accordance with the physique of the patient P.

The controlling function 238b is configured to speculate the spectrum reconstruction possible region corresponding to the patient, on the basis of the output values related to the energy spectra. In other words, the controlling function 238b determines the spectrum reconstruction possible region corresponding to the patient on the basis of the output values related to the energy spectra. In one example, when the chart illustrated in FIG. 15 has been generated by the calculating function 238a, the controlling function 238b determines an output value Th to be a threshold value as indicated in FIG. 15. In this situation, for example, when the X-ray tube voltage is 120 kVp, there should not be any photon having an energy level exceeding 120 keV, in theory. For this reason, it is also acceptable to consider the region exceeding 120 keV as a pile up and to set the threshold value at 120 keV. Alternatively, it is also acceptable to set a threshold value to permit any values equal to or higher than a certain count rate, on the basis of a time constant of the circuit, or the like.

After that, within the reconstruction region, the controlling function 238b speculates such a region in which the output values corresponding to all the views are each equal to or smaller than the predetermined threshold value to be a spectrum reconstruction possible region. For example, as illustrated in the chart G1 in FIG. 15, because the output values in the position P11 are each equal to or smaller than the threshold values in all the view directions, the controlling function 238b speculates the position P11 to be in the spectrum reconstruction possible region. Further, as illustrated in the chart G2 in FIG. 15, because the output values in the position P12 are not each equal to or smaller than the threshold value in all the view directions, the controlling function 238b speculates the position P12 not to be in the spectrum reconstruction possible region. Also, with respect to each of the positions (pixels) other than the position P11 and the position P12, the controlling function 238b judges whether or not the output values are each equal to or smaller than the threshold value with respect to the pieces of projection data corresponding to all the views.

Further, generally speaking, the count rate is lower at the center of a scan FOV, and the closer a position is to the outer edge of the scan FOV, the higher the count rate is. For this reason, for example, the controlling function 238b may divide the scan FOV region into a center region and an outer edge region, for example, so as to perform the judging process while selectively focusing on a region where the energy spectra concerning a pile-up or the like may be inaccurate with respect to the outer edge region. Alternatively, for example, the controlling function 238b may draw a concentric circle on the center of the scan FOV to determine an arbitrary position on the concentric circle as a representative point and may further judge whether or not the output value in the representative point is equal to or smaller than the threshold value. Further, when the output value exceeds the threshold value in a certain position, the controlling function 238b speculates that the region positioned on the outside of the concentric circle including the position is a region on which the spectrum reconstructing process shall not be performed. In that situation, the calculating function 238a may calculate the output value by obtaining the X-ray spectrum only from the representative point, without calculating the output values from all the positions.

Figure 16:
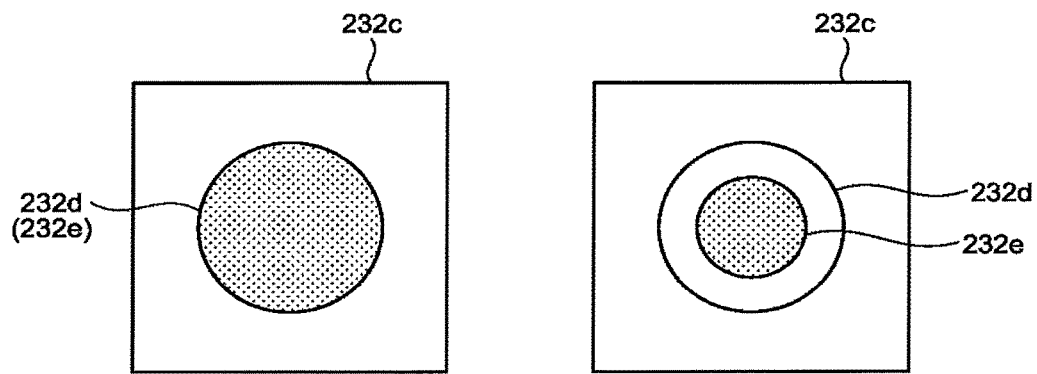
FIG. 16 is yet another drawing for explaining the second embodiment.

Further, the controlling function 238b causes the display 232 to display the spectrum reconstruction possible region. In FIG. 16, for the sake of convenience in the explanation, only one (i.e., the display region 232c) of the plurality of display regions into which the display 232 is divided is illustrated. Further, for example, FIG. 16 illustrates the reconstruction region 232d and a spectrum reconstruction possible region 232e with respect to a cross-sectional plane of interest selected in the two-dimensional scanogram. In the left section of FIG. 16, the reconstruction region 232d and the spectrum reconstruction possible region 232e are the same as each other. For example, when having speculated that, in the entire region of the reconstruction region 232d, the output values corresponding to all the views are each equal to or smaller than the predetermined threshold value, the controlling function 238b causes the display 232 to display, in the display region 232c, the spectrum reconstruction possible region 232e that is identical to the reconstruction region 232d, as illustrated in the left section of FIG. 16.

In the right section of FIG. 16, a partial region of the reconstruction region 232d is determined as the spectrum reconstruction possible region 232e. For example, when having speculated that, in the partial region of the reconstruction region 232d, the output values corresponding to all the views are each equal to or smaller than the predetermined threshold value, the controlling function 238b causes the display 232 to display the spectrum reconstruction possible region 232e, which is the partial region of the reconstruction region 232d, as illustrated in the right section of FIG. 16.

The receiving function 238c receives, from the operator, the setting about the speculated spectrum reconstruction possible region. In this situation, the receiving function 238c receives at least one selected from between an operation to determine the spectrum reconstruction possible region and an operation to change the spectrum reconstruction possible region, as the setting about the speculated spectrum reconstruction possible region.

Figure 17:
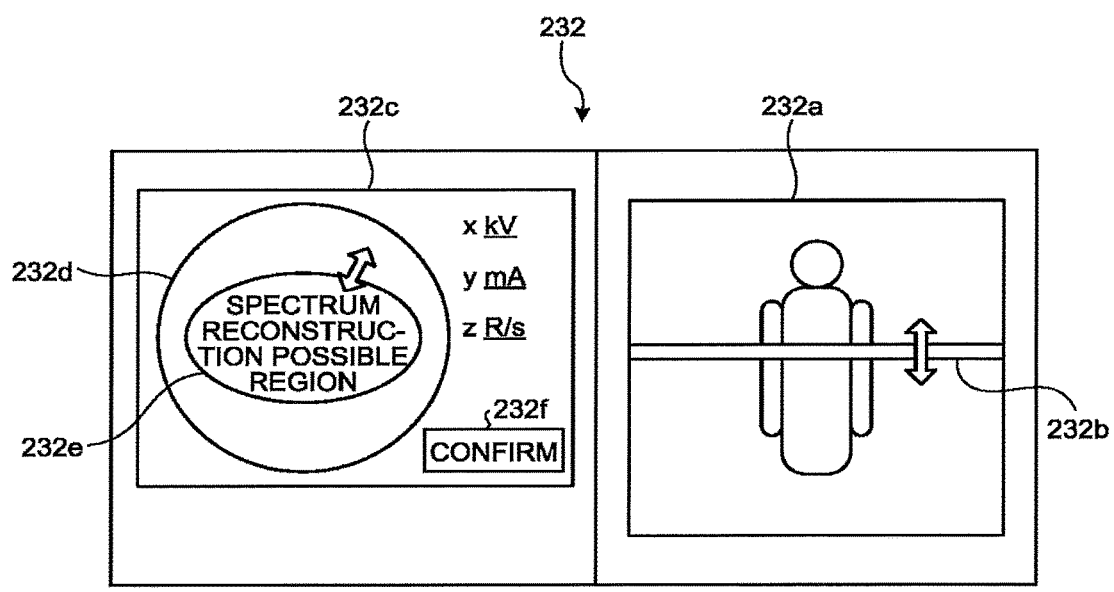
FIG. 17 is yet another drawing for explaining the second embodiment.

FIG. 17 illustrates an example in which the display 232 is divided into two sections, namely the display region 232a and the display region 232c. In the display region 232a of FIG. 17, the two-dimensional scanogram taken while the X-ray tube 212 is in the 0-degree position is displayed. Further, with reference to FIG. 17, a situation will be explained in which the operator has selected the cross-sectional plane of interest 232b from the two-dimensional scanogram. In that situation, in the display region 232c of the display 232, the reconstruction region 232d, the spectrum reconstruction possible region 232e, and the parameters of the scan conditions are displayed. FIG. 17 illustrates an example in which, as the parameters of the scan conditions, the X-ray tube voltage x (kV), the X-ray tube current y (mA), and the rotation speed z (R/s) are displayed. Further, as illustrated in FIG. 17, in the display region 232c of the display 232, a confirm button 232f is displayed.

In this situation, for example, the operator refers to the reconstruction region 232d and the spectrum reconstruction possible region 232e illustrated in FIG. 17 and checks to see whether or not the spectrum reconstruction possible region 232e includes the region he/she wishes to view. After that, when having determined that the spectrum reconstruction possible region 232e includes the region he/she wishes to view, the operator selects the confirm button 232f. When having received the selection of the confirm button 232f, the receiving function 238c determines that an operation to determine the spectrum reconstruction possible region has been received. As a result, the conditions for the main scan have been confirmed.

Further, the operator performs an operation to change the spectrum reconstruction possible region 232e. For example, when having determined that the spectrum reconstruction possible region 232e does not include the region he/she wishes to view, the operator performs an operation to change the spectrum reconstruction possible region 232e. More specifically, when having determined that the spectrum reconstruction possible region 232e illustrated in FIG. 17 is too small to include the region he/she wishes to view, the operator selects the boundary line of the spectrum reconstruction possible region 232e within the display region 232c and performs an operation to enlarge the spectrum reconstruction possible region 232e. In this manner, the receiving function 238c receives the setting to enlarge the spectrum reconstruction possible region from the operator.

In contrast, even when a partial region of the reconstruction region 232d is determined to be the spectrum reconstruction possible region 232e, if the viewer wishes to view a small region such as a region of the heart, the speculated spectrum reconstruction possible region 232e may be too large, in some situations. In those situations, the operator selects the boundary line of the spectrum reconstruction possible region 232e within the display region 232c and performs an operation to reduce the spectrum reconstruction possible region 232e. In this manner, the receiving function 238c receives the setting to reduce the spectrum reconstruction possible region from the operator.

Further, the controlling function 238b sets parameters of the scan conditions in accordance with the change made to the spectrum reconstruction possible region 232e. In other words, the controlling function 238b sets the parameters used for newly scanning the spectrum reconstruction possible region 232e that was set and further causes the display 232 to display the set parameters. In other words, the controlling function 238b identifies the parameters used for scanning the spectrum reconstruction possible region that was set and further causes a display to display the identified parameters. For example, in accordance with the enlargement of the spectrum reconstruction possible region, the controlling function 238b sets a parameter so as to decrease the X-ray radiation dose per unit time period. On the contrary, in accordance with the reduction of the spectrum reconstruction possible region, the controlling function 238b sets a parameter so as to increase the X-ray radiation dose per unit time period.

More specifically, when enlarging the spectrum reconstruction possible region, the controlling function 238b establishes settings to lower the gantry rotation speed and to decrease the X-ray tube current. On the contrary, when reducing the spectrum reconstruction possible region, the controlling function 238b establishes settings to raise the gantry rotation speed and to increase the X-ray tube current. Among the parameters of the scan conditions, one or more parameters to be changed may be designated in advance or one or more parameters of which the setting values are fixed with a higher priority may be designated in advance. For example, as a scan condition suitable for an organ with movements such as the heart, the controlling function 238b sets a higher gantry rotation speed. Alternatively, parameters of scan conditions corresponding to each scan target may be stored as pre-set parameters.

Further, although the example was explained in which the receiving function 238c receives the change made to the spectrum reconstruction possible region 232e, possible embodiments are not limited to this example. For instance, the receiving function 238c may receive a change made to any of the parameters. More specifically, the receiving function 238c may be configured to receive an operation to change the numerical value of any of the X-ray tube voltage x (kV), the X-ray tube current y (mA), and the rotation speed z (R/s). In that situation, the calculating function 238a calculates the output values corresponding to all the views, on the basis of the parameters of the scan conditions resulting from the change. For example, the calculating function 238a estimates the X-ray spectra corresponding to the views on the basis of the parameters of the scan conditions resulting from the change and further calculates the output values. After that, the controlling function 238b speculates a spectrum reconstruction possible region corresponding to the patient on the basis of the output values related to the energy spectra and further causes the display 232 to display the speculated spectrum reconstruction possible region. In other words, the controlling function 238b causes the display 232 to display the spectrum reconstruction possible region that was changed in accordance with the change made to the parameters.

Figure 18:
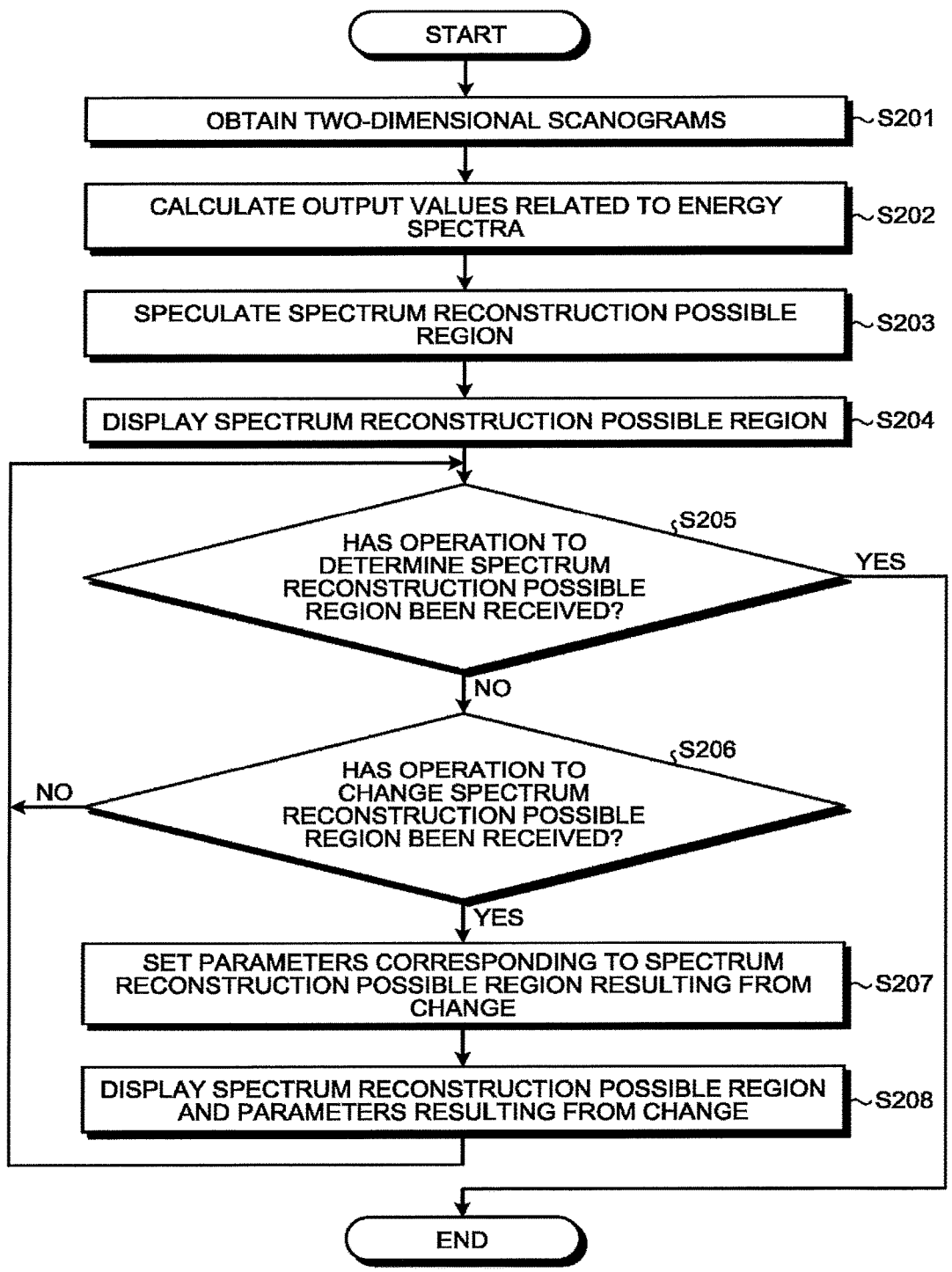
FIG. 18 is a flowchart illustrating a processing procedure to speculate a spectrum reconstruction possible region performed by the X-ray CT apparatus according to the second embodiment.

Next, a processing procedure performed by the X-ray CT apparatus according to the second embodiment to speculate the spectrum reconstruction possible region will be explained, with reference to FIG. 18. FIG. 18 is a flowchart illustrating the processing procedure to speculate the spectrum reconstruction possible region performed by the X-ray CT apparatus according to the second embodiment. Steps S201 and S202 are steps corresponding to the calculating function 238a. As a result of the system controlling circuitry 238 invoking and executing a predetermined program recorded in the system controlling circuitry 238, the calculating function 238a is realized. At step S201, the calculating function 238a obtains one or more two-dimensional scanograms. For example, the calculating function 238a obtains a two-dimensional scanogram taken while the X-ray tube 212 is in the 0-degree position and a two-dimensional scanogram taken while the X-ray tube 212 is in the 90-degree position.

At step S202, the calculating function 238a calculates output values related to energy spectra from the two-dimensional scanograms. For example, the calculating function 238a calculates, for each of the views, the output values in the image on the basis of the X-ray spectra.

Steps S203 and S204 and steps S207 and S208 are steps corresponding to the controlling function 238b. As a result of the system controlling circuitry 238 invoking and executing a predetermined program recorded in the system controlling circuitry 238, the controlling function 238b is realized. At step S203, the controlling function 238b speculates a spectrum reconstruction possible region. For example, the controlling function 238b speculates, within the reconstruction region, such a region in which the output values corresponding to all views are each equal to or smaller than the predetermined threshold value to be the spectrum reconstruction possible region.

At step S204, the controlling function 238b causes the display 232 to display the spectrum reconstruction possible region. For example, the controlling function 238b causes the display 232 to display the reconstruction region, the spectrum reconstruction possible region, and the parameters of the scan conditions.

Steps S205 and S206 are steps corresponding to the receiving function 238c. As a result of the system controlling circuitry 238 invoking and executing a predetermined program recorded in the system controlling circuitry 238, the receiving function 238c is realized. At step S205, the receiving function 238c judges whether or not an operation to determine the spectrum reconstruction possible region has been received. For example, when having received, from the operator, an operation to select the confirm button 232f illustrated in FIG. 17, the receiving function 238c determines that an operation to determine the spectrum reconstruction possible region is received. In this situation, when having determined that an operation to determine the spectrum reconstruction possible region is received (step S205: Yes), the receiving function 238c ends the process.

On the contrary, when having determined that an operation to determine the spectrum reconstruction possible region is not received (step S205: No), the receiving function 238c proceeds to step S206. After that, at step S206, the receiving function 238c judges whether or not an operation to change the spectrum reconstruction possible region has been received. For example, when having received, from the operator, an operation to change the spectrum reconstruction possible region 232e illustrated in FIG. 17, the receiving function 238c determines that an operation to change the spectrum reconstruction possible region is received. In this situation, when having determined that an operation to change the spectrum reconstruction possible region is not received (step S206: No), the receiving function 238c proceeds to step S205 and continues to judge whether or not an operation to determine the spectrum reconstruction possible region has been received.

On the contrary, when having determined that an operation to change the spectrum reconstruction possible region is received (step S206: Yes), the receiving function 238c proceeds to step S207. At step S207, the controlling function 238b sets parameters of the scan conditions corresponding to the spectrum reconstruction possible region resulting from the change. For example, in accordance with an enlargement of the spectrum reconstruction possible region, the controlling function 238b sets a parameter so as to decrease the X-ray radiation dose per unit time period. On the contrary, in accordance with a reduction of the spectrum reconstruction possible region, the controlling function 238b sets a parameter so as to increase the X-ray radiation dose per unit time period.

After that, at step S208, the controlling function 238b causes the display 232 to display the spectrum reconstruction possible region resulting from the change and the parameters of the scan conditions resulting from the change. For example, the controlling function 238b causes the display 232 to display the reconstruction region, the spectrum reconstruction possible region resulting from the change, and the parameters of the scan conditions resulting from the change. After the process at step S208 is finished, the procedure proceeds to step S205 where the receiving function 238c judges whether an operation to determine the spectrum reconstruction possible region has been received.

As explained above, the X-ray CT apparatus according to the second embodiment is configured to calculate the output values related to the energy spectra from the image of the patient obtained by scanning the patient with the X-rays. After that, the X-ray CT apparatus according to the second embodiment is configured to speculate a spectrum reconstruction possible region corresponding to the patient on the basis of the output values related to the energy spectra and to further cause the display 232 to display the spectrum reconstruction possible region.

In other words, in the second embodiment, during the scanogram taking process performed prior to the main scan, a region is estimated where the output values of the energy spectra will each be equal to or larger than the threshold value, so that the region where it is possible to reconstruct a substance discriminatory image can be displayed over the scan FOV. With these arrangements, according to the second embodiment, for example, the operator is able to understand the spectrum reconstruction possible region before performing the main scan.

Further, when the spectrum reconstruction possible region fails to cover the area intended by the operator, the operator adjusts the scan conditions so as to include the intended area. For example, the operator may perform an operation to enlarge or reduce the spectrum reconstruction possible region. In that situation, in accordance with the enlargement of the spectrum reconstruction possible region, the X-ray CT apparatus according to the second embodiment sets a parameter of the scan conditions so as to decrease the X-ray radiation dose per unit time period. On the contrary, in accordance with the reduction of the spectrum reconstruction possible region, the X-ray CT apparatus according to the second embodiment sets a parameter of the scan conditions so as to increase the X-ray radiation dose per unit time period.

As a result, according to the second embodiment, it is possible to set an optimal spectrum reconstruction possible region. Further, according to the second embodiment, because it is possible to set the optimal spectrum reconstruction possible region prior to performing the main scan, it is possible to reduce the situations where the image taking process needs to be performed again. Further, because the main scan is performed after setting the optimal spectrum reconstruction possible region, the image reconstructing circuitry 236 is able to generate a spectrum reconstruction image having a high level of precision. As a result, according to the second embodiment, it is possible to perform a diagnosis process accurately. In this situation, the spectrum reconstruction image may be, for example, a substance discriminatory image, a monochrome X-ray image, or the like.

Further, with respect to the region within the scan FOV other than the spectrum reconstruction possible region, the image reconstructing circuitry 236 generates a reconstruction image by using the energy integral values. In this manner, the image reconstructing circuitry 236 is also able to improve the processing speed of the reconstructing process.

A Modification Example of the Second Embodiment

In the second embodiment above, the example is explained in which the candidate region in which the spectrum reconstructing process is possible is speculated by using the one threshold value; however, possible embodiments are not limited to this example. For instance, another arrangement is acceptable in which a candidate region in which the spectrum reconstructing process is possible is speculated by using two or more threshold values. In the following sections, an example will be explained in which two threshold values, namely a first threshold value and a second threshold value, are used.

Figure 19:
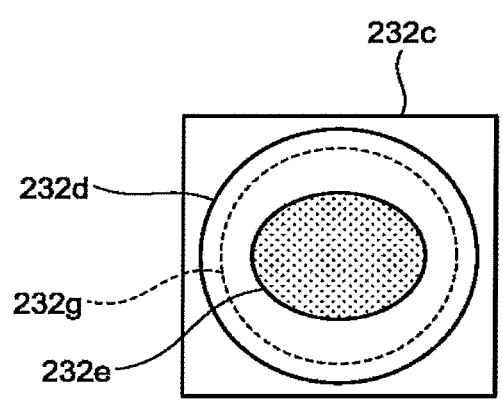
FIG. 19 is a drawing for explaining a modification example of the second embodiment.

The first threshold value is the threshold value explained in the second embodiment. In other words, the first threshold value is used for speculating the output values to be in a spectrum reconstruction possible region. The second threshold value is set to a value larger than the first threshold value. The second threshold value is used for speculating a candidate region in which the spectrum reconstructing process becomes possible when the output values are corrected. Further, for example, the controlling function 238b further speculates the candidate region in which the spectrum reconstructing process becomes possible when the output values are corrected and further causes the display 232 to display the speculated candidate region. FIG. 19 is a drawing for explaining the modification example of the second embodiment.

For the sake of convenience in the explanation, FIG. 19 illustrates only one (the display region 232c) of the plurality of display regions into which the display 232 is divided. Further, FIG. 19 illustrates the reconstruction region 232d, the spectrum reconstruction possible region 232e, and a candidate region 232g with respect to a cross-sectional plane of interest selected in a two-dimensional scanogram, for example.

In FIG. 19, a partial region of the reconstruction region 232d is determined as the spectrum reconstruction possible region 232e. For example, within the reconstruction region 232d, the controlling function 238b speculates such a region in which the output values corresponding to all the views are each equal to or smaller than the first threshold value to be the spectrum reconstruction possible region 232e, as illustrated in FIG. 19. Further, within the reconstruction region 232d, the controlling function 238b speculates such a region in which the output values corresponding to all the views are not each equal to or smaller than the first threshold value but are each equal to or smaller than the second threshold value, to be the candidate region 232g.

As explained above, in the modification example of the second embodiment, in addition to the spectrum reconstruction possible region, the candidate region is set in which the spectrum reconstructing process becomes possible when the output values are corrected. With this arrangement, according to the modification example of the second embodiment, it is possible to set the spectrum reconstruction possible region in a larger area prior to performing the main scan. As a result, even when a region having a large area is to be scanned, it is possible to generate a spectrum reconstruction image.

Third Embodiment

The controlling function 238b may speculate a plurality of spectrum reconstruction possible regions, set parameters of the scan conditions to newly scan the spectrum reconstruction possible regions, and cause the display 232 to display the speculated spectrum reconstruction possible regions and the parameters of the scan conditions corresponding to the spectrum reconstruction possible regions.

Figure 20:
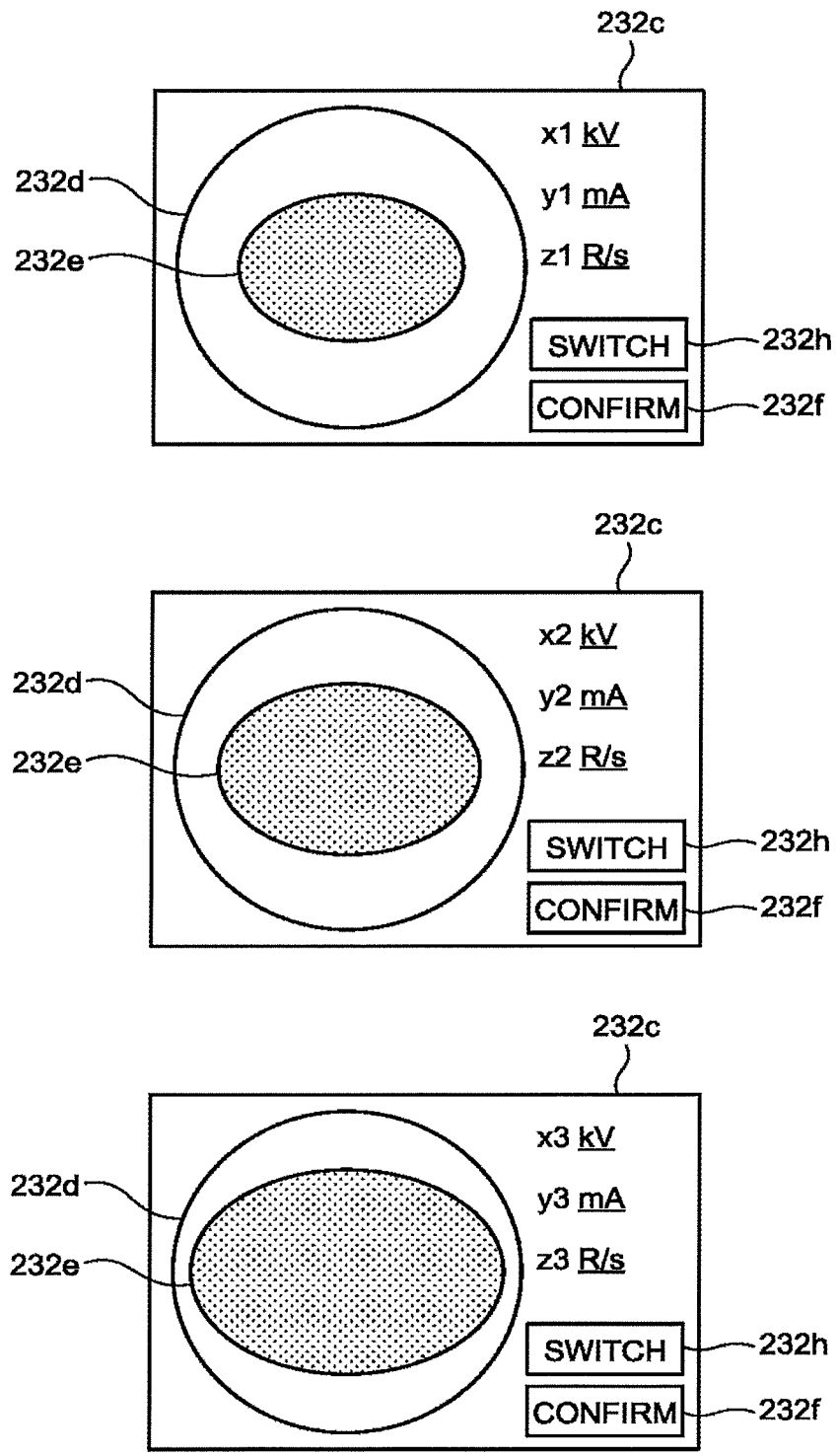
FIG. 20 is a drawing for explaining a third embodiment.

FIG. 20 is a drawing for explaining a third embodiment. With reference to FIG. 20, an example will be explained in which the display 232 displays, in a predetermined order, three combinations of spectrum reconstruction possible regions and parameters of scan conditions corresponding to the spectrum reconstruction possible regions. For example, when having speculated a plurality of spectrum reconstruction possible regions, the controlling function 238b, at first, causes the display 232 to display the combination illustrated in the top section of FIG. 20. For the sake of convenience in the explanation, FIG. 20 illustrates only one (the display region 232c) of the plurality of display regions into which the display 232 is divided. Further, in the example in FIG. 20, in the display region 232c of the display 232, the reconstruction region 232d, the spectrum reconstruction possible region 232e, the parameters of the scan conditions, the confirm button 232f, and a switch button 232h are displayed. The reconstruction region 232d illustrated in FIG. 20 is a cross-sectional plane of interest selected in a two-dimensional scanogram, for example.

The spectrum reconstruction possible region 232e illustrated in the top section of FIG. 20 has the smallest region among the three combinations. In this situation, when the operator selects the switch button 232h, the receiving function 238c receives a setting to change the spectrum reconstruction possible region from the operator. Further, for example, the controlling function 238b causes the display 232 to display the combination illustrated in the middle section of FIG. 20.

The spectrum reconstruction possible region 232e illustrated in the middle section of FIG. 20 is larger than the spectrum reconstruction possible region 232e illustrated in the top section of FIG. 20. In this situation, when the operator selects the switch button 232h, the receiving function 238c receives a setting to change the spectrum reconstruction possible region from the operator. After that, for example, the controlling function 238b causes the display 232 to display the combination illustrated in the bottom section of FIG. 20.

The spectrum reconstruction possible region 232e illustrated in the bottom section of FIG. 20 has the largest region among the three combinations. In this situation, when the operator selects the switch button 232h, the receiving function 238c receives a setting to change the spectrum reconstruction possible region from the operator. Further, for example, the controlling function 238b causes the display 232 to display the combination illustrated in the top section of FIG. 20. In FIG. 20, when the operator selects the confirm button 232f, the receiving function 238c determines that an operation to determine the spectrum reconstruction possible region has been received.

In this manner, in the third embodiment, the plurality of spectrum reconstruction possible regions are speculated, so that the display 232 displays, in the predetermined order, the combinations of the spectrum reconstruction possible regions and the parameters of the scan conditions corresponding to the spectrum reconstruction possible regions. With this arrangement, the operator is able to understand the plurality of spectrum reconstruction possible regions prior to performing the main scan. As a result, according to the third embodiment, the operator is able to select a spectrum reconstruction possible region suitable for a diagnosis process, from among the plurality of combinations. Further, according to the third embodiment, because it is possible to set the optimal spectrum reconstruction possible region prior to performing the main scan, it is possible to reduce the situations where the image taking process needs to be performed again. Further, because the main scan is performed after setting the optimal spectrum reconstruction possible region, the image reconstructing circuitry 236 is able to generate a spectrum reconstruction image having a high level of precision. Consequently, according to the third embodiment, it is possible to perform a diagnosis process accurately.

In the third embodiment, the example is explained in which the display 232 displays, in the predetermined order, the three combinations of the spectrum reconstruction possible regions and the parameters of the scan conditions corresponding to the spectrum reconstruction possible regions; however, possible embodiments are not limited to this example. For instance, the controlling function 238b may cause the display 232 to display the three combinations side by side. Further, when causing the display 232 to display the three combinations side by side, the controlling function 238b may have the three combinations displayed in mutually-different colors or may arrange a recommended combination among the three combinations to be displayed in a highlighted manner. Further, the number of combinations to be displayed is not limited to three and may arbitrarily be set.

Further, in the third embodiment, the receiving function 238c may receive a setting to enlarge or reduce the spectrum reconstruction possible regions from the operator, similarly to the second embodiment. Further, the controlling function 238b accordingly receives the setting to enlarge or reduce the spectrum reconstruction possible regions from the operator.

Other Embodiments

It is possible to carry out the present disclosure in various different modes other than those described in the embodiments above.

In the embodiments described above, the example is explained in which, within the reconstruction region, the controlling function 238b speculates such a region in which the output values corresponding to all the views are each equal to or smaller than the threshold value, to be the spectrum reconstruction possible region; however, possible embodiments are not limited to this example. For instance, within the reconstruction region, the controlling function 238b may speculate such a region in which the output values corresponding to views in a range that make a half reconstruction process possible are each equal to or smaller than a threshold value, to be a spectrum reconstruction possible region.

Further, in the embodiments described above, the example is explained in which the calculating function 238a obtains the two-dimensional scanogram taken from at least one direction as the image; however, possible embodiments are not limited to this example. For instance, as the image, the calculating function 238a may obtain an image acquired in a main scan performed in the past (e.g., an image taken in the previously-performed medical examination). In that situation, the calculating function 238a calculates actual measured values of the projection data as output values. In other words, the image acquired in the main scan performed in the past serves as an example of the imaging planning-purpose image.

Further, in the embodiments described above, the example is explained in which the X-ray CT apparatus takes the two-dimensional scanograms; however, another arrangement is acceptable in which, for example, when the X-ray CT apparatus has taken a three-dimensional scanogram image (a three-dimensional scanogram), the calculating function 238a obtains the three-dimensional scanogram as the image. In that situation, during a scanogram image taking process, the scan controlling circuitry 233 takes the three-dimensional scanogram image by acquiring projection data corresponding to the entire circumference around the patient. For example, the scan controlling circuitry 233 may acquire the projection data corresponding to the entire circumference around the patient by performing a helical scan or a non-helical scan. In this situation, the scan controlling circuitry 233 performs either the helical scan or the non-helical scan on a large area such as the entire chest, the entire abdomen, the entire upper body, the entire body, or the like of the patient, by using a radiation dose lower than that used in the main image taking process. As the non-helical scan, for example, a scan implementing the step-and-shoot method described above may be performed. In this manner, when the scan controlling circuitry 233 has acquired the projection data corresponding to the entire circumference around the patient, the image reconstructing circuitry 236 is able to reconstruct three-dimensional X-ray CT image data (volume data). Thus, by using the reconstructed volume data, it is possible to generate a position determining image from an arbitrary direction. Whether the position determining image is to be taken two-dimensionally or three-dimensionally may arbitrarily be selected by the operator or may be set in advance in accordance with specifics of the medical examination.

Further, the functions of the calculating function 238a, the controlling function 238b, and the receiving function 238c explained in the above embodiments may be realized by using software. For example, the functions of the calculating function 238a, the controlling function 238b, and the receiving function 238c are realized as a result of causing a computer to execute a spectrum reconstruction possible region speculating program that defines the processing procedure described in the embodiments above as being performed by the calculating function 238a, the controlling function 238b, and the receiving function 238c. The spectrum reconstruction possible region speculating program is, for example, stored in a hard disk, a semiconductor memory element, or the like and is read and executed by a processor such as a Central Processing Unit (CPU), a Micro Processing Unit (MPU), or the like. Further, the spectrum reconstruction possible region speculating program may be distributed as being recorded an a computer-readable recording medium such as a Compact Disc Read-Only Memory (CD-ROM), a Magnetic Optical (MO) disk, a Digital Versatile Disk (DVD), or the like.

Further, the judging function 371, the determining function 372, and the display controlling function 373 explained in the above embodiments may be realized by using software. For example, the judging function 371, the determining function 372, and the display controlling function 373 are realized as a result of causing a computer to execute a program that defines the processing procedure described in the embodiments above as being performed by the judging function 371, the determining function 372, and the display controlling function 373. The program is, for example, stored in a hard disk, a semiconductor memory element, or the like and is read and executed by a processor such as a CPU, an MPU, or the like. Further, the program may be distributed as being recorded an a computer-readable recording medium such as a Compact Disc Read-Only Memory (CD-ROM), a Magnetic Optical (MO) disk, a Digital Versatile Disk (DVD), or the like.

The term "processor" used in the above explanation denotes, for example, a Central Processing Unit (CPU), a Graphics Processing Unit (GPU), or a circuit such as an Application Specific Integrated Circuit (ASIC) or a programmable logic device (e.g., a Simple Programmable Logic Device [SPLD], a Complex Programmable Logic Device [CPLD], or a Field Programmable Gate Array [FPGA]). The processors realize the functions thereof by reading and executing the program incorporated in the circuit thereof. Further, instead of having the program incorporated in the circuit of each of the processors, it is also acceptable to have the programs stored in a storage circuit included in the console 30 or 230. In that situation, each of the processors realizes the function thereof by reading and executing the program stored in the storage circuit. The processors according to the present embodiments each do not necessarily have to individually be configured as a single circuit; it is acceptable to structure one processor by combining together a plurality of independent circuits, so as to realize the functions thereof. Further, it is also acceptable to integrate two or more of the constituent elements illustrated in FIG. 1 or 10 into one processor so as to realize the functions thereof.

The constituent elements of the apparatuses and the devices illustrated in the drawings in the embodiments and the modification examples above are based on functional concepts. Thus, it is not necessary to physically configure the constituent elements as indicated in the drawings. In other words, the specific modes of distribution and integration of the apparatuses and the devices are not limited to those illustrated in the drawings. It is acceptable to functionally or physically distribute or integrate all or a part of the apparatuses and the devices in any arbitrary units, depending on various loads and the status of use. For example, the processing circuitry 37 may have functions of the image reconstructing circuitry 36. Further, all or an arbitrary part of the processing functions performed by the apparatuses and the devices may be realized by a CPU and a computer program analyzed and executed by the CPU or may be realized as hardware using wired logic.

Further, it is possible to realize the controlling method explained in the embodiments above, by causing a computer such as a personal computer or a workstation to execute a control computer program (hereinafter, "control program") prepared in advance. It is possible to distribute the control program via a network such as the Internet. Further, the control program may be executed as being recorded on a computer-readable recording medium such as a hard disk, a flexible disk (FD), a CD-ROM, an MO disk, a DVD, or the like and being read from the recording medium by a computer.

Further, with regard to the processes explained in the embodiments and the modification examples above, it is also acceptable to manually perform all or a part of the processes described as being performed automatically. Conversely, by using a method that is publicly known, it is also acceptable to automatically perform all or a part of the processes described as being performed manually. Further, unless noted otherwise, it is acceptable to arbitrarily modify any of the processing procedures, the controlling procedures, specific names, and various information including various types of data and parameters that are presented in the above text and the drawings.

According to at least one aspect of the embodiments described above, it is possible to improve the precision level and the processing speed of the image reconstructing processes in the photon counting CT procedure.

In addition, according to at least one aspect of the embodiments described above, it is possible to set the optimal spectrum reconstruction possible region.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray CT apparatus comprising:
an X-ray tube configured to generate X-rays;
a photon counting detector including a plurality of detecting elements each configured to output a signal in response to any of the X-rays becoming incident thereto after having passed through an examined subject; and
processing circuitry configured to:
determine, within a reconstruction region, a first region on which a spectrum reconstructing process is to be performed and a second region on which an energy integral reconstructing process is to be performed, on a basis of output values related to energy spectra based on signals output by the detecting elements; and
generate an image on a basis of the determined first region and the determined second region.

2. The X-ray CT apparatus according to claim 1, wherein the processing circuitry calculates the output values for each of views and judges, for each of the views, whether or not the calculated output values are each equal to or larger than a threshold value, and
with respect to each of positions included in the reconstruction region, the processing circuitry determines the first region and the second region on a basis of judgment results regarding the views going through the position.

3. The X-ray CT apparatus according to claim 2, wherein, with respect to each of the positions included in the reconstruction region, the processing circuitry determines the position to be in the first region when the output values corresponding to all the views going through the position are each smaller than the threshold value.

4. The X-ray CT apparatus according to claim 2, wherein with respect to each of the positions included in the reconstruction region, the processing circuitry determines the position to be in the first region when, among all the views going through the position, the output values corresponding to views in such a quantity that make a half reconstruction process possible are each smaller than the threshold value, and the processing circuitry generates a first image corresponding to the first region by performing the half reconstruction process.

5. The X-ray CT apparatus according to claim 2, wherein from among the views of which the output values are determined to be equal to or larger than the threshold value, the processing circuitry determines a position including a view that makes a spectrum reconstructing process possible when the output value thereof is corrected, to be in a third region, and after correcting the output values in the third region, the processing circuitry generates a third image corresponding to the third region by performing the spectrum reconstructing process.

6. The X-ray CT apparatus according to claim 2, wherein, within the reconstruction region, the processing circuitry determines such a region that is positioned outside a view of which the output value is determined to be equal to or larger than the threshold value, to be the second region.

7. The X-ray CT apparatus according to claim 1, wherein the processing circuitry determines a region having either a circular shape or an oval shape, to be the first region.

8. The X-ray CT apparatus according to claim 1, wherein the processing circuitry further causes a first image corresponding to the first region to be displayed as being superimposed over a second image corresponding to the second region.

9. The X-ray CT apparatus according to claim 8, wherein the processing circuitry causes the first image corresponding to the first region and the second image corresponding to the second region to be displayed in such a manner that the first and the second images are distinguishable from each other.

10. The X-ray CT apparatus according to claim 1, wherein the processing circuitry calculates total output values of counts of energy bins as the output values.

11. The X-ray CT apparatus according to claim 1, wherein the processing circuitry calculates pile-up count values of counts of energy bins as the output values.

12. The X-ray CT apparatus according to claim 1, wherein the processing circuitry calculates energy integral values of representative values of energy bins as the output values.

13. The X-ray CT apparatus according to claim 1, wherein the processing circuitry calculates pile-up energy integral values of representative values of energy bins as the output values.

14. A reconstruction processing apparatus comprising processing circuitry configured to:

obtain output values related to energy spectra based on signals output from a plurality of detecting elements included in a photon counting detector and each configured to output a signal in response to X-rays becoming incident thereto after having passed through an examined subject;

determine, within a reconstruction region, a first region on which a spectrum reconstructing process is to be performed and a second region on which an energy integral reconstruction process is to be performed, on a basis of the output values; and generate an image on a basis of the determined first region and the determined second region.

15. An X-ray CT apparatus comprising processing circuitry configured to:

calculate output values related to energy spectra from an imaging planning-purpose image obtained by imaging an examined subject while using X-rays; and determine a spectrum reconstruction possible region corresponding to the examined subject, on a basis of the output values related to the energy spectra and to cause a display to display the spectrum reconstruction possible region.

16. The X-ray CT apparatus according to claim 15, wherein the processing circuitry further receives, from an operator, a setting regarding the spectrum reconstruction possible region that was speculated, and the processing circuitry identifies a parameter used when the set spectrum reconstruction possible region is scanned and causes a display to display the identified parameter.

17. The X-ray CT apparatus according to claim 16, wherein the processing circuitry receives, from the operator, a setting to either enlarge or reduce the spectrum reconstruction possible region, and in accordance with the enlargement of the spectrum reconstruction possible region, the processing circuitry sets the parameter so as to decrease an X-ray radiation dose per unit time period, whereas in accordance with the reduction of the spectrum reconstruction possible region, the processing circuitry sets the parameter so as to increase the X-ray radiation dose per unit time period.

18. The X-ray CT apparatus according to claim 15, wherein the processing circuitry speculates two or more of the spectrum reconstruction possible regions, sets parameters used for newly scanning the spectrum reconstruction possible regions, and causes a display to display the speculated spectrum reconstruction possible regions and the parameters corresponding to the spectrum reconstruction possible regions.

19. The X-ray CT apparatus according to claim 15, wherein the processing circuitry calculates the output values in the imaging planning-purpose image for each of views and calculates output values corresponding to all the views on a basis of the calculated output values corresponding to each image, and within the reconstruction region, the processing circuitry speculates such a region in which the output values corresponding to all the views are each equal to or smaller than a predetermined threshold value, to be the spectrum reconstruction possible region.

20. The X-ray CT apparatus according to claim 15, wherein the processing circuitry calculates the output values in the image for each of views and calculates output values corresponding to all the views on a basis of the calculated output values corresponding to each image, and within the reconstruction region, the processing circuitry speculates such a region in which the output values corresponding to views in a certain range that make a half reconstruction process possible are each equal to or smaller than a predetermined threshold value, to be the spectrum reconstruction possible region.

* * * * *